(12) United States Patent
Morishita et al.

(10) Patent No.: US 7,994,151 B2
(45) Date of Patent: Aug. 9, 2011

(54) COMPOSITIONS AND METHODS FOR ANGIOGENIC THERAPY UTILIZING GENES ENCODING ETS-1

(75) Inventors: Ryuichi Morishita, Osaka (JP); Hiromi Koike, Osaka (JP); Tadashi Tanabe, Osaka (JP); Motokuni Aoki, Hyogo (JP)

(73) Assignee: Anges MG, Inc., Osaka (JP)

( * ) Notice: Subject to any disclaimer, the term of this patent is extended or adjusted under 35 U.S.C. 154(b) by 129 days.

(21) Appl. No.: 12/435,335

(22) Filed: May 4, 2009

(65) Prior Publication Data

US 2010/0240735 A1    Sep. 23, 2010

Related U.S. Application Data

(62) Division of application No. 10/312,435, filed as application No. PCT/JP01/05514 on Jun. 27, 2001, now abandoned.

(30) Foreign Application Priority Data

Jun. 27, 2000  (JP) ................................ 2000-192480
Dec. 21, 2000  (JP) ................................ 2000-388624

(51) Int. Cl.
*A61K 48/00* (2006.01)
*A01N 63/00* (2006.01)
*A01N 65/00* (2006.01)
*C12N 15/00* (2006.01)
*C07H 21/04* (2006.01)

(52) U.S. Cl. .................. 514/44 R; 424/93.1; 435/320.1; 536/23.5

(58) Field of Classification Search .................. None
See application file for complete search history.

(56) References Cited

U.S. PATENT DOCUMENTS

| | | | |
|---|---|---|---|
| 5,785,965 A | 7/1998 | Pratt | |
| 5,814,509 A | 9/1998 | Tanabe | |
| 5,830,879 A | 11/1998 | Isner | |
| 6,723,702 B2 | 4/2004 | Conrad et al. | |
| 6,814,539 B2 | 11/2004 | Farnsworth et al. | |
| 7,276,594 B1 | 10/2007 | Mori et al. | |
| 2003/0219380 A1* | 11/2003 | Fong et al. ..................... | 424/9.1 |

FOREIGN PATENT DOCUMENTS

| | | |
|---|---|---|
| DE | 19940012 A1 | 3/2001 |
| EP | 727490 | 8/1996 |
| WO | WO 95/30013 A1 | 11/1995 |
| WO | WO 97/14307 A1 | 4/1997 |
| WO | WO 00/02589 A1 | 1/2000 |

OTHER PUBLICATIONS

Sato (2001) "Role of ETS Family Transcription Factors in Vascular Development and Angiogenesis", Cell Structure and Function, 26: 19-24.*

Aoki, M., et al., "Angiogenesis induced by hepatocyte growth factor in non-infarcted myocardium and infarcted myocardium: up-regulation of essential transcription factor for angiogenesis, ets," *Gene Therapy*, vol. 7(5), pp. 417-427 (Mar. 2000).
Bowie, et al., "Deciphering the message in protein sequences: tolerance to amino acid substitutions," 1990, Science, 247: 1306-10.
Cheng et al., 2000, J. Forms. Med. Assoc., 99(8): 603-11. (Abstract Only Provided).
Deonarain, "Ligand-targeted receptor-mediated vectors for gene delivery," 1998, Exp. Opin. Ther. Pat., 8(1): 53-69.
Eck, et al., 1996, Goodman & Gilman's The Pharacological Basis of Therapeutics, 9th Ed., McGraw-Hill, New York, NY, pp. 77-101.
Gorecki, "Prospects and problems of gene therapy: an update," 2001, Exp. Opin. Emerging Drugs, 6(2); 187-98.
He, H., et al., "Vascular Endothelial Growth Factor Signals Endothelial Cell Production of Nitric Oxide and Prostacyclin through Flk-1/KDR Activation of c-Src," 1999, J. Biol. Chem., vol. 274, No. 35, pp. 25130-25135.
Ibukiyama, 1996, Jpn. Heart J., 37(3):385-300. (Abstract Only Provided).
Iwasaka, Chika et al.; "Ets-1 Regulates Angiogenesis by Inducing the Expression of Urokinase-Type Plasminogen Activator and Matrix Metalloproteinase-1 and the Migration of Vascular Endothelial Cells"; 1996, *Journal of Cellular Physiology*, vol. 169, pp. 522-531.
Jones, M.K., et al., "Inhibition of angiogenesis by nonsteroidal anti-inflammatory drugs: insight into mechanisms and implications for cancer growth and ulcer healing," 1999, Nat. Med., vol. 5, No. 12, pp. 1418-1423.
Koike et al., Co-Tranfection of Human Prostacyclin Synthase (PGIS) Gene with Hepacyte Growth2000, Circulation, 102(18 Supp.): 224.
Langer, et al., "Where a pill won't reach," 2003, Scientific American, 288(4): 50-57.
Liu et al., "Efficacy of combination gene therapy with multiple growth factor cDNAs to enhance skin flap survival in a rat model," 2005, DNA Cell. Biol., 24(11): 751-57. (Abstract Only Provided).
Rudinger, "Characteristics of the amino acids as components of a peptide hormone sequence,"1976, Peptide Hormones, University Park Press, Baltimore, MD., pp. 1-7.
Sato, Y., "Transcription Factor ETS-1 as a Molecular Target for Angiogenesis Inhibition," *Human Cell*, vol. 11(4), pp. 207-214 (Dec. 1998).

(Continued)

*Primary Examiner* — Robert M Kelly
(74) *Attorney, Agent, or Firm* — Kilpatrick Townsend & Stockton LLP

(57) ABSTRACT

The present invention provides: (1) pharmaceutical compositions for angiogenic therapy which contain, as the active ingredients, at least one substance selected from substances having vasodilating effect and/or platelet aggregation inhibitory effect, and substances producing them; and a gene encoding an angiogenesis factor; (2) agents for potentiating the angiogenic effect of a gene encoding an angiogenesis factor that contain, as the active ingredient, at least one substance selected from substances having vasodilating effect and/or platelet aggregation inhibitory effect and substances producing them; (3) an angiogenic agent which contains a prostacyclin synthase gene as the active ingredient; (4) pharmaceutical compositions for angiogenic therapy which contain ets-1 gene and another gene encoding an angiogenesis factor as the active ingredients; (4) an agent which contain ets 1 gene as the active ingredient for potentiating the angiogenic effect of another gene encoding an angiogenesis factor; and (5) an angiogenic agent which contains ets-1 gene as the active ingredient.

12 Claims, 13 Drawing Sheets

OTHER PUBLICATIONS

Schratzberger, et al., "Therapeutic angiogenesis by gene transfer in critical limb and myocardial ischemia," 2003, Curr. Pharm. Des., 9: 1041-47.

Tsujii, Masahiko, "COX for Kekkan Shinsei," Igaku no. Ayumi, Apr. 2000, vol. 193, No. 245-248.

Valter, M., et al., "Expression of the Ets-1 Transcription Factor in Human Astrocytomas is Associated with Fms-like Tyrosine Kinase-1 (Flt-1)/Vascular Endothelial Growth Factor Receptor-1 Synthesis and Neoangiogenesis," *Cancer Research*, vol. 59(21), pp. 5608-5614 (Nov. 1, 1999).

Vassali, Giuseppe and David A. Dichek; "Gene therapy for arterial thrombosis"; *Cardiovascular Research*; 1997; pp. 459-469; vol. 35; Elsevier Science B.V.

Verma et al., "Gene therapy-promises, problems and prospects," 1997, Nature, 389: 239-42.

Watson, D., et al., "Mammalian *ets-1* and *ets-2* genes encode highly conserved proteins," *Proc. Natl. Acad. Sci. USA*, vol. 85(21), pp. 7862-7866 (Nov. 1988).

Xin et al., "Hepatocyte Growth Factor Enhances Vascular Endothelial Growth Factor-Induced Angiogenesis in Vitro and in Vivo," 2001, Am. J. Pathol., 158(3): 1111-20.

Fujitani, K. et al., "Clinical evaluation on combined administration of oral prostacyclin analogue beraprost and phosphodiesterase inhibitor cilostazol," 1995, Pharmacol Res. 31(2), 121-125.

Nakamura, et al., "Molecular cloning and expression of human hepatocyte growth factor," Nov. 23, 1989, Nature, 342(6248): 440-443.

* cited by examiner

SEQUENCE LISTING

```
<160> NUMBER OF SEQ ID NOS: 4

<210> SEQ ID NO 1
<211> LENGTH: 2576
<212> TYPE: DNA
<213> ORGANISM: Homo sapiens
<220> FEATURE:
<223> OTHER INFORMATION: human hepatocyte growth factor (HGF, hHGF)
<220> FEATURE:
<221> NAME/KEY: CDS
<222> LOCATION: (102)..(2288)
<223> OTHER INFORMATION: HGF

<400> SEQUENCE: 1
gggctcagag ccgactggct cttttaggca ctgactccga acaggattct ttcacccagg      60
catctcctcc agagggatcc gccagcccgt ccagcagcac c atg tgg gtg acc aaa     116
                                              Met Trp Val Thr Lys
                                                1               5 ctc ctg cca gcc ctg ctg ctg cag cat gtc ctc ctg cat ctc ctc ctg      164
Leu Leu Pro Ala Leu Leu Leu Gln His Val Leu Leu His Leu Leu Leu
                10                  15                  20 ctc ccc atc gcc atc ccc tat gca gag gga caa agg aaa aga aga aat      212
Leu Pro Ile Ala Ile Pro Tyr Ala Glu Gly Gln Arg Lys Arg Arg Asn
            25                  30                  35 aca att cat gaa ttc aaa aaa tca gca aag act acc cta atc aaa ata      260
Thr Ile His Glu Phe Lys Lys Ser Ala Lys Thr Thr Leu Ile Lys Ile
        40                  45                  50 gat cca gca ctg aag ata aaa acc aaa aaa gtg aat act gca gac caa      308
Asp Pro Ala Leu Lys Ile Lys Thr Lys Lys Val Asn Thr Ala Asp Gln
    55                  60                  65 tgt gct aat aga tgt act agg aat aaa gga ctt cca ttc act tgc aag      356
Cys Ala Asn Arg Cys Thr Arg Asn Lys Gly Leu Pro Phe Thr Cys Lys
70                  75                  80                  85 gct ttt gtt ttt gat aaa gca aga aaa caa tgc ctc tgg ttc ccc ttc      404
Ala Phe Val Phe Asp Lys Ala Arg Lys Gln Cys Leu Trp Phe Pro Phe
                90                  95                  100 aat agc atg tca agt gga gtg aaa aaa gaa ttt ggc cat gaa ttt gac      452
Asn Ser Met Ser Ser Gly Val Lys Lys Glu Phe Gly His Glu Phe Asp
            105                 110                 115 ctc tat gaa aac aaa gac tac att aga aac tgc atc att ggt aaa gga      500
Leu Tyr Glu Asn Lys Asp Tyr Ile Arg Asn Cys Ile Ile Gly Lys Gly
        120                 125                 130
```

```
cgc agc tac aag gga aca gta tct atc act aag agt ggc atc aaa tgt        548
Arg Ser Tyr Lys Gly Thr Val Ser Ile Thr Lys Ser Gly Ile Lys Cys
    135                 140                 145 cag ccc tgg agt tcc atg ata cca cac gaa cac agc ttt ttg cct tcg        596
Gln Pro Trp Ser Ser Met Ile Pro His Glu His Ser Phe Leu Pro Ser
150                 155                 160                 165 agc tat cgg ggt aaa gac cta cag gaa aac tac tgt cga aat cct cga        644
Ser Tyr Arg Gly Lys Asp Leu Gln Glu Asn Tyr Cys Arg Asn Pro Arg
                170                 175                 180 ggg gaa gaa ggg gga ccc tgg tgt ttc aca agc aat cca gag gta cgc        692
Gly Glu Glu Gly Gly Pro Trp Cys Phe Thr Ser Asn Pro Glu Val Arg
            185                 190                 195 tac gaa gtc tgt gac att cct cag tgt tca gaa gtt gaa tgc atg acc        740
Tyr Glu Val Cys Asp Ile Pro Gln Cys Ser Glu Val Glu Cys Met Thr
        200                 205                 210 tgc aat ggg gag agt tat cga ggt ctc atg gat cat aca gaa tca ggc        788
Cys Asn Gly Glu Ser Tyr Arg Gly Leu Met Asp His Thr Glu Ser Gly
    215                 220                 225 aag att tgt cag cgc tgg gat cat cag aca cca cac cgg cac aaa ttc        836
Lys Ile Cys Gln Arg Trp Asp His Gln Thr Pro His Arg His Lys Phe
230                 235                 240                 245 ttg cct gaa aga tat ccc gac aag ggc ttt gat gat aat tat tgc cgc        884
Leu Pro Glu Arg Tyr Pro Asp Lys Gly Phe Asp Asp Asn Tyr Cys Arg
                250                 255                 260 aat ccc gat ggc cag ccg agg cca tgg tgt tat act ctt gac cct cac        932
Asn Pro Asp Gly Gln Pro Arg Pro Trp Cys Tyr Thr Leu Asp Pro His
            265                 270                 275 acc cgc tgg gag tac tgt gca att aaa aca tgc gct gac aat act atg        980
Thr Arg Trp Glu Tyr Cys Ala Ile Lys Thr Cys Ala Asp Asn Thr Met
        280                 285                 290 aat gac act gat gtt cct ttg gaa aca act gaa tgc atc caa ggt caa       1028
Asn Asp Thr Asp Val Pro Leu Glu Thr Thr Glu Cys Ile Gln Gly Gln
    295                 300                 305 gga gaa ggc tac agg ggc act gtc aat acc att tgg aat gga att cca       1076
Gly Glu Gly Tyr Arg Gly Thr Val Asn Thr Ile Trp Asn Gly Ile Pro
310                 315                 320                 325 tgt cag cgt tgg gat tct cag tat cct cac gag cat gac atg act cct       1124
Cys Gln Arg Trp Asp Ser Gln Tyr Pro His Glu His Asp Met Thr Pro
                330                 335                 340 gaa aat ttc aag tgc aag gac cta cga gaa aat tac tgc cga aat cca       1172
Glu Asn Phe Lys Cys Lys Asp Leu Arg Glu Asn Tyr Cys Arg Asn Pro
            345                 350                 355 gat ggg tct gaa tca ccc tgg tgt ttt acc act gat cca aac atc cga       1220
Asp Gly Ser Glu Ser Pro Trp Cys Phe Thr Thr Asp Pro Asn Ile Arg
        360                 365                 370 gtt ggc tac tgc tcc caa att cca aac tgt gat atg tca cat gga caa       1268
Val Gly Tyr Cys Ser Gln Ile Pro Asn Cys Asp Met Ser His Gly Gln
    375                 380                 385 gat tgt tat cgt ggg aat ggc aaa aat tat atg ggc aac tta tcc caa       1316
Asp Cys Tyr Arg Gly Asn Gly Lys Asn Tyr Met Gly Asn Leu Ser Gln
390                 395                 400                 405 aca aga tct gga cta aca tgt tca atg tgg gac aag aac atg gaa gac       1364
Thr Arg Ser Gly Leu Thr Cys Ser Met Trp Asp Lys Asn Met Glu Asp
                410                 415                 420 tta cat cgt cat atc ttc tgg gaa cca gat gca agt aag ctg aat gag       1412
Leu His Arg His Ile Phe Trp Glu Pro Asp Ala Ser Lys Leu Asn Glu
            425                 430                 435 aat tac tgc cga aat cca gat gat gat gct cat gga ccc tgg tgc tac       1460
Asn Tyr Cys Arg Asn Pro Asp Asp Asp Ala His Gly Pro Trp Cys Tyr
        440                 445                 450
```

| | | |
|---|---|---|
| acg gga aat cca ctc att cct tgg gat tat tgc cct att tct cgt tgt<br>Thr Gly Asn Pro Leu Ile Pro Trp Asp Tyr Cys Pro Ile Ser Arg Cys<br>455                   460                 465 | | 1508 |
| gaa ggt gat acc aca cct aca ata gtc aat tta gac cat ccc gta ata<br>Glu Gly Asp Thr Thr Pro Thr Ile Val Asn Leu Asp His Pro Val Ile<br>470                 475                480               485 | | 1556 |
| tct tgt gcc aaa acg aaa caa ttg cga gtt gta aat ggg att cca aca<br>Ser Cys Ala Lys Thr Lys Gln Leu Arg Val Val Asn Gly Ile Pro Thr<br>               490                495               500 | | 1604 |
| cga aca aac ata gga tgg atg gtt agt ttg aga tac aga aat aaa cat<br>Arg Thr Asn Ile Gly Trp Met Val Ser Leu Arg Tyr Arg Asn Lys His<br>               505                510               515 | | 1652 |
| atc tgc gga gga tca ttg ata aag gag agt tgg gtt ctt act gca cga<br>Ile Cys Gly Gly Ser Leu Ile Lys Glu Ser Trp Val Leu Thr Ala Arg<br>             520                525               530 | | 1700 |
| cag tgt ttc cct tct cga gac ttg aaa gat tat gaa gct tgg ctt gga<br>Gln Cys Phe Pro Ser Arg Asp Leu Lys Asp Tyr Glu Ala Trp Leu Gly<br>               535                540               545 | | 1748 |
| att cat gat gtc cac gga aga gga gat gag aaa tgc aaa cag gtt ctc<br>Ile His Asp Val His Gly Arg Gly Asp Glu Lys Cys Lys Gln Val Leu<br>550                   555                560               565 | | 1796 |
| aat gtt tcc cag ctg gta tat ggc cct gaa gga tca gat ctg gtt tta<br>Asn Val Ser Gln Leu Val Tyr Gly Pro Glu Gly Ser Asp Leu Val Leu<br>               570                575               580 | | 1844 |
| atg aag ctt gcc agg cct gct gtc ctg gat gat ttt gtt agt acg att<br>Met Lys Leu Ala Arg Pro Ala Val Leu Asp Asp Phe Val Ser Thr Ile<br>               585                590               595 | | 1892 |
| gat tta cct aat tat gga tgc aca att cct gaa aag acc agt tgc agt<br>Asp Leu Pro Asn Tyr Gly Cys Thr Ile Pro Glu Lys Thr Ser Cys Ser<br>             600                605               610 | | 1940 |
| gtt tat ggc tgg ggc tac act gga ttg atc aac tat gat ggc cta tta<br>Val Tyr Gly Trp Gly Tyr Thr Gly Leu Ile Asn Tyr Asp Gly Leu Leu<br>             615                620               625 | | 1988 |
| cga gtg gca cat ctc tat ata atg gga aat gag aaa tgc agc cag cat<br>Arg Val Ala His Leu Tyr Ile Met Gly Asn Glu Lys Cys Ser Gln His<br>630                   635                640               645 | | 2036 |
| cat cga ggg aag gtg act ctg aat gag tct gaa ata tgt gct ggg gct<br>His Arg Gly Lys Val Thr Leu Asn Glu Ser Glu Ile Cys Ala Gly Ala<br>             650                655               660 | | 2084 |
| gaa aag att gga tca gga cca tgt gag ggg gat tat ggt ggc cca ctt<br>Glu Lys Ile Gly Ser Gly Pro Cys Glu Gly Asp Tyr Gly Gly Pro Leu<br>             665                670               675 | | 2132 |
| gtt tgt gag caa cat aaa atg aga atg gtt ctt ggt gtc att gtt cct<br>Val Cys Glu Gln His Lys Met Arg Met Val Leu Gly Val Ile Val Pro<br>             680                685               690 | | 2180 |
| ggt cgt gga tgt gcc att cca aat cgt cct ggt att ttt gtc cga gta<br>Gly Arg Gly Cys Ala Ile Pro Asn Arg Pro Gly Ile Phe Val Arg Val<br>695                   700                705 | | 2228 |
| gca tat tat gca aaa tgg ata cac aaa att att tta aca tat aag gta<br>Ala Tyr Tyr Ala Lys Trp Ile His Lys Ile Ile Leu Thr Tyr Lys Val<br>710                   715                720               725 | | 2276 |
| cca cag tca tag ctgaagtaag tgtgtctgaa gcacccacca atacaactgt<br>Pro Gln Ser | | 2328 |
| cttttacatg aagatttcag agaatgtgga atttaaaatg tcacttacaa caatcctaag | | 2388 |
| acaactactg gagagtcatg tttgttgaaa ttctcattaa tgtttatggg tgttttctgt | | 2448 |
| tgttttgttt gtcagtgtta ttttgtcaat gttgaagtga attaaggtac atgcaagtgt | | 2508 |
| aataacatat ctcctgaaga tacttgaatg gattaaaaaa acacacaggt atatttgctg | | 2568 | gatgataa 2576

<210> SEQ ID NO 2
<211> LENGTH: 728
<212> TYPE: PRT
<213> ORGANISM: Homo sapiens
<220> FEATURE:
<223> OTHER INFORMATION: human hepatocyte growth factor (HGF, hHGF)

<400> SEQUENCE: 2

```
Met Trp Val Thr Lys Leu Leu Pro Ala Leu Leu Leu Gln His Val Leu
 1               5                  10                  15

Leu His Leu Leu Leu Leu Pro Ile Ala Ile Pro Tyr Ala Glu Gly Gln
             20                  25                  30

Arg Lys Arg Arg Asn Thr Ile His Glu Phe Lys Lys Ser Ala Lys Thr
         35                  40                  45

Thr Leu Ile Lys Ile Asp Pro Ala Leu Lys Ile Lys Thr Lys Lys Val
     50                  55                  60

Asn Thr Ala Asp Gln Cys Ala Asn Arg Cys Thr Arg Asn Lys Gly Leu
 65                  70                  75                  80

Pro Phe Thr Cys Lys Ala Phe Val Phe Asp Lys Ala Arg Lys Gln Cys
                 85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asn Cys
        115                 120                 125

Ile Ile Gly Lys Gly Arg Ser Tyr Lys Gly Thr Val Ser Ile Thr Lys
    130                 135                 140

Ser Gly Ile Lys Cys Gln Pro Trp Ser Ser Met Ile Pro His Glu His
145                 150                 155                 160

Ser Phe Leu Pro Ser Ser Tyr Arg Gly Lys Asp Leu Gln Glu Asn Tyr
                165                 170                 175

Cys Arg Asn Pro Arg Gly Glu Glu Gly Gly Pro Trp Cys Phe Thr Ser
            180                 185                 190

Asn Pro Glu Val Arg Tyr Glu Val Cys Asp Ile Pro Gln Cys Ser Glu
        195                 200                 205

Val Glu Cys Met Thr Cys Asn Gly Glu Ser Tyr Arg Gly Leu Met Asp
    210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
            260                 265                 270

Thr Leu Asp Pro His Thr Arg Trp Glu Tyr Cys Ala Ile Lys Thr Cys
        275                 280                 285

Ala Asp Asn Thr Met Asn Asp Thr Asp Val Pro Leu Glu Thr Thr Glu
    290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
                325                 330                 335

His Asp Met Thr Pro Glu Asn Phe Lys Cys Lys Asp Leu Arg Glu Asn
            340                 345                 350

Tyr Cys Arg Asn Pro Asp Gly Ser Glu Ser Pro Trp Cys Phe Thr Thr
        355                 360                 365
```

```
Asp Pro Asn Ile Arg Val Gly Tyr Cys Ser Gln Ile Pro Asn Cys Asp
    370                 375                 380
Met Ser His Gly Gln Asp Cys Tyr Arg Gly Asn Gly Lys Asn Tyr Met
385                 390                 395                 400
Gly Asn Leu Ser Gln Thr Arg Ser Gly Leu Thr Cys Ser Met Trp Asp
                405                 410                 415
Lys Asn Met Glu Asp Leu His Arg His Ile Phe Trp Glu Pro Asp Ala
            420                 425                 430
Ser Lys Leu Asn Glu Asn Tyr Cys Arg Asn Pro Asp Asp Ala His
        435                 440                 445
Gly Pro Trp Cys Tyr Thr Gly Asn Pro Leu Ile Pro Trp Asp Tyr Cys
    450                 455                 460
Pro Ile Ser Arg Cys Glu Gly Asp Thr Thr Pro Thr Ile Val Asn Leu
465                 470                 475                 480
Asp His Pro Val Ile Ser Cys Ala Lys Thr Lys Gln Leu Arg Val Val
                485                 490                 495
Asn Gly Ile Pro Thr Arg Thr Asn Ile Gly Trp Met Val Ser Leu Arg
            500                 505                 510
Tyr Arg Asn Lys His Ile Cys Gly Gly Ser Leu Ile Lys Glu Ser Trp
        515                 520                 525
Val Leu Thr Ala Arg Gln Cys Phe Pro Ser Arg Asp Leu Lys Asp Tyr
    530                 535                 540
Glu Ala Trp Leu Gly Ile His Asp Val His Gly Arg Gly Asp Glu Lys
545                 550                 555                 560
Cys Lys Gln Val Leu Asn Val Ser Gln Leu Val Tyr Gly Pro Glu Gly
                565                 570                 575
Ser Asp Leu Val Leu Met Lys Leu Ala Arg Pro Ala Val Leu Asp Asp
            580                 585                 590
Phe Val Ser Thr Ile Asp Leu Pro Asn Tyr Gly Cys Thr Ile Pro Glu
        595                 600                 605
Lys Thr Ser Cys Ser Val Tyr Gly Trp Gly Tyr Thr Gly Leu Ile Asn
    610                 615                 620
Tyr Asp Gly Leu Leu Arg Val Ala His Leu Tyr Ile Met Gly Asn Glu
625                 630                 635                 640
Lys Cys Ser Gln His His Arg Gly Lys Val Thr Leu Asn Glu Ser Glu
                645                 650                 655
Ile Cys Ala Gly Ala Glu Lys Ile Gly Ser Gly Pro Cys Glu Gly Asp
            660                 665                 670
Tyr Gly Gly Pro Leu Val Cys Glu Gln His Lys Met Arg Met Val Leu
        675                 680                 685
Gly Val Ile Val Pro Gly Arg Gly Cys Ala Ile Pro Asn Arg Pro Gly
    690                 695                 700
Ile Phe Val Arg Val Ala Tyr Tyr Ala Lys Trp Ile His Lys Ile Ile
705                 710                 715                 720
Leu Thr Tyr Lys Val Pro Gln Ser
                725

<210> SEQ ID NO 3
<211> LENGTH: 1977
<212> TYPE: DNA
<213> ORGANISM: Homo sapiens
<220> FEATURE:
<223> OTHER INFORMATION: human prostaglandin I-2 (PGI-2, prostacyclin)
      synthase (PGIS)
<220> FEATURE:
<221> NAME/KEY: CDS
```

<222> LOCATION: (28)..(1530)
<223> OTHER INFORMATION: PGIS

<400> SEQUENCE: 3

```
agccccgcca gccccgccag ccccgcg atg gct tgg gcc gcg ctc ctc ggc ctc        54
                              Met Ala Trp Ala Ala Leu Leu Gly Leu
                                1               5 ctg gcc gca ctg ttg ctg ctg cta ctg agc cgc cgc cgc acg cgg             102
Leu Ala Ala Leu Leu Leu Leu Leu Leu Ser Arg Arg Arg Thr Arg
 10                  15                  20                  25 cga cct ggt gag cct ccc ctg gac ctg ggc agc atc ccc tgg ttg ggg         150
Arg Pro Gly Glu Pro Pro Leu Asp Leu Gly Ser Ile Pro Trp Leu Gly
                 30                  35                  40 tat gcc ttg gac ttt gga aaa gat gct gcc agc ttc ctc acg agg atg         198
Tyr Ala Leu Asp Phe Gly Lys Asp Ala Ala Ser Phe Leu Thr Arg Met
             45                  50                  55 aag gag aag cac ggt gac atc ttt act ata ctg gtt ggg ggc agg tat         246
Lys Glu Lys His Gly Asp Ile Phe Thr Ile Leu Val Gly Gly Arg Tyr
         60                  65                  70 gtc acc gtt ctc ctg gac cca cac tcc tac gac gcg gtg gtg tgg gag         294
Val Thr Val Leu Leu Asp Pro His Ser Tyr Asp Ala Val Val Trp Glu
 75                  80                  85 cct cgc acc agg ctc gac ttc cat gcc tat gcc atc ttc ctc atg gag         342
Pro Arg Thr Arg Leu Asp Phe His Ala Tyr Ala Ile Phe Leu Met Glu
 90                  95                 100                 105 agg att ttt gat gtg cag ctt cca cat tac agc ccc agt gat gaa aag         390
Arg Ile Phe Asp Val Gln Leu Pro His Tyr Ser Pro Ser Asp Glu Lys
                110                 115                 120 gcc agg atg aaa ctg act ctt ctc cac aga gag ctc cag gca ctc aca         438
Ala Arg Met Lys Leu Thr Leu Leu His Arg Glu Leu Gln Ala Leu Thr
            125                 130                 135 gaa gcc atg tat acc aac ctc cat gca gtg ctg ttg ggc gat gct aca         486
Glu Ala Met Tyr Thr Asn Leu His Ala Val Leu Leu Gly Asp Ala Thr
        140                 145                 150 gaa gca ggc agt ggc tgg cac gag atg ggt ctc ctc gac ttc tcc tac         534
Glu Ala Gly Ser Gly Trp His Glu Met Gly Leu Leu Asp Phe Ser Tyr
    155                 160                 165 agc ttc ctg ctc aga gcc ggc tac ctg act ctt tac gga att gag gcg         582
Ser Phe Leu Leu Arg Ala Gly Tyr Leu Thr Leu Tyr Gly Ile Glu Ala
170                 175                 180                 185 ctg cca cgc acc cat gaa agc cag gcc cag gac cgc gtc cac tca gct         630
Leu Pro Arg Thr His Glu Ser Gln Ala Gln Asp Arg Val His Ser Ala
                190                 195                 200 gat gtc ttc cac acc ttt cgc cag ctc gac cgg ctg ctc ccc aaa ctg         678
Asp Val Phe His Thr Phe Arg Gln Leu Asp Arg Leu Leu Pro Lys Leu
            205                 210                 215 gcc cgt ggc tcc ctg tca gtg ggg gac aag gac cac atg tgc agt gtc         726
Ala Arg Gly Ser Leu Ser Val Gly Asp Lys Asp His Met Cys Ser Val
        220                 225                 230 aaa agt cgc ctg tgg aag ctg cta tcc cca gcc agg ctg gcc agg cgg         774
Lys Ser Arg Leu Trp Lys Leu Leu Ser Pro Ala Arg Leu Ala Arg Arg
    235                 240                 245 gcc cac cgg agc aaa tgg ctg gag agt tac ctg ctg cac ctg gag gag         822
Ala His Arg Ser Lys Trp Leu Glu Ser Tyr Leu Leu His Leu Glu Glu
250                 255                 260                 265 atg ggt gtg tca gag gag atg cag gca cgg gcc ctg gtg ctg cag ctg         870
Met Gly Val Ser Glu Glu Met Gln Ala Arg Ala Leu Val Leu Gln Leu
                270                 275                 280 tgg gcc aca cag ggg aat atg ggt ccc gct gcc ttc tgg ctc ctg ctc         918
Trp Ala Thr Gln Gly Asn Met Gly Pro Ala Ala Phe Trp Leu Leu Leu
            285                 290                 295
```

-continued

```
ttc ctt ctc aag aat cct gaa gcc ctg gct gct gtc cgc gga gag ctc        966
Phe Leu Leu Lys Asn Pro Glu Ala Leu Ala Ala Val Arg Gly Glu Leu
            300                 305                 310 gag agt atc ctt tgg caa gcg gag cag cct gtc tcg cag acg acc act       1014
Glu Ser Ile Leu Trp Gln Ala Glu Gln Pro Val Ser Gln Thr Thr Thr
        315                 320                 325 ctc cca cag aag gtt cta gac agc aca cct gtg ctt gat agc gtg ctg       1062
Leu Pro Gln Lys Val Leu Asp Ser Thr Pro Val Leu Asp Ser Val Leu
330                 335                 340                 345 agt gag agc ctc agg ctt aca gct gcc ccc ttc atc acc cgc gag gtt       1110
Ser Glu Ser Leu Arg Leu Thr Ala Ala Pro Phe Ile Thr Arg Glu Val
                350                 355                 360 gtg gtg gac ctg gcc atg ccc atg gca gac ggg aga gaa ttc aac ctg       1158
Val Val Asp Leu Ala Met Pro Met Ala Asp Gly Arg Glu Phe Asn Leu
            365                 370                 375 cga cgt ggt gac cgc ctc ctc ctc ttc ccc ttc ctg agc ccc cag aga       1206
Arg Arg Gly Asp Arg Leu Leu Leu Phe Pro Phe Leu Ser Pro Gln Arg
        380                 385                 390 gac cca gaa atc tac aca gac cca gag gta ttt aaa tac aac cga ttc       1254
Asp Pro Glu Ile Tyr Thr Asp Pro Glu Val Phe Lys Tyr Asn Arg Phe
395                 400                 405 ctg aac cct gac gga tca gag aag aaa gac ttt tac aag gat ggg aaa       1302
Leu Asn Pro Asp Gly Ser Glu Lys Lys Asp Phe Tyr Lys Asp Gly Lys
410                 415                 420                 425 cgg ctg aag aat tac aac atg ccc tgg ggg gcg ggg cac aat cac tgc       1350
Arg Leu Lys Asn Tyr Asn Met Pro Trp Gly Ala Gly His Asn His Cys
                430                 435                 440 ctg ggg agg agt tat gcg gtc aac agc atc aaa caa ttt gtg ttc ctt       1398
Leu Gly Arg Ser Tyr Ala Val Asn Ser Ile Lys Gln Phe Val Phe Leu
            445                 450                 455 gtg ctg gtg cac ttg gac ttg gag ctg atc aac gca gat gtg gag atc       1446
Val Leu Val His Leu Asp Leu Glu Leu Ile Asn Ala Asp Val Glu Ile
        460                 465                 470 cct gag ttt gac ctc agc agg tac ggc ttc ggt ctg atg cag ccg gaa       1494
Pro Glu Phe Asp Leu Ser Arg Tyr Gly Phe Gly Leu Met Gln Pro Glu
    475                 480                 485 cac gac gtg ccc gtc cgc tac cgc atc cgc cca tga cacagggagc            1540
His Asp Val Pro Val Arg Tyr Arg Ile Arg Pro
490                 495                 500 agatggatcc acgtgctcgc ctctgcccag cctgccccag cctgccccag cctcccagct    1600
ttctgtgtgc acagttggcc cgggtgcagg tgctagcatt accacttccc tgcttttctc    1660
ccagaaggct gggtccaggg gagggaaaag ctaagagggt gaacaaagaa aagacattga    1720
aagctctatg gattatccac tgcaaagttt tctttccaaa atcaggcttt gtctgctccc    1780
aattcacctc gttactctca cctcgtgata tccacaaatg ctattcagat aaggcagaac    1840
taggagtctt cactgctctg cccccaactc ccggaggtgt caccttccta gttcttatga    1900
gctagcatgg cccgggcctt atccagtcaa agcggatgct ggccacagaa aggccactca    1960
ggatgtcctt tgtgtcc                                                    1977
```

<210> SEQ ID NO 4
<211> LENGTH: 500
<212> TYPE: PRT
<213> ORGANISM: Homo sapiens
<220> FEATURE:
<223> OTHER INFORMATION: human prostaglandin I-2 (PGI-2, prostacyclin) synthase (PGIS)

<400> SEQUENCE: 4

-continued

```
Met Ala Trp Ala Ala Leu Leu Gly Leu Leu Ala Ala Leu Leu Leu Leu
 1               5                  10                  15

Leu Leu Leu Ser Arg Arg Thr Arg Pro Gly Glu Pro Pro Leu
             20                  25                  30

Asp Leu Gly Ser Ile Pro Trp Leu Gly Tyr Ala Leu Asp Phe Gly Lys
             35                  40                  45

Asp Ala Ala Ser Phe Leu Thr Arg Met Lys Glu Lys His Gly Asp Ile
 50                  55                  60

Phe Thr Ile Leu Val Gly Gly Arg Tyr Val Thr Val Leu Leu Asp Pro
 65                  70                  75                  80

His Ser Tyr Asp Ala Val Val Trp Glu Pro Arg Thr Arg Leu Asp Phe
                 85                  90                  95

His Ala Tyr Ala Ile Phe Leu Met Glu Arg Ile Phe Asp Val Gln Leu
                100                 105                 110

Pro His Tyr Ser Pro Ser Asp Glu Lys Ala Arg Met Lys Leu Thr Leu
            115                 120                 125

Leu His Arg Glu Leu Gln Ala Leu Thr Glu Ala Met Tyr Thr Asn Leu
    130                 135                 140

His Ala Val Leu Leu Gly Asp Ala Thr Glu Ala Gly Ser Gly Trp His
145                 150                 155                 160

Glu Met Gly Leu Leu Asp Phe Ser Tyr Ser Phe Leu Leu Arg Ala Gly
                165                 170                 175

Tyr Leu Thr Leu Tyr Gly Ile Glu Ala Leu Pro Arg Thr His Glu Ser
                180                 185                 190

Gln Ala Gln Asp Arg Val His Ser Ala Asp Val Phe His Thr Phe Arg
            195                 200                 205

Gln Leu Asp Arg Leu Leu Pro Lys Leu Ala Arg Gly Ser Leu Ser Val
    210                 215                 220

Gly Asp Lys Asp His Met Cys Ser Val Lys Ser Arg Leu Trp Lys Leu
225                 230                 235                 240

Leu Ser Pro Ala Arg Leu Ala Arg Arg Ala His Arg Ser Lys Trp Leu
                245                 250                 255

Glu Ser Tyr Leu Leu His Leu Glu Glu Met Gly Val Ser Glu Glu Met
                260                 265                 270

Gln Ala Arg Ala Leu Val Leu Gln Leu Trp Ala Thr Gln Gly Asn Met
            275                 280                 285

Gly Pro Ala Ala Phe Trp Leu Leu Leu Phe Leu Leu Lys Asn Pro Glu
    290                 295                 300

Ala Leu Ala Ala Val Arg Gly Glu Leu Glu Ser Ile Leu Trp Gln Ala
305                 310                 315                 320

Glu Gln Pro Val Ser Gln Thr Thr Thr Leu Pro Gln Lys Val Leu Asp
                325                 330                 335

Ser Thr Pro Val Leu Asp Ser Val Leu Ser Glu Ser Leu Arg Leu Thr
                340                 345                 350

Ala Ala Pro Phe Ile Thr Arg Glu Val Val Val Asp Leu Ala Met Pro
            355                 360                 365

Met Ala Asp Gly Arg Glu Phe Asn Leu Arg Arg Gly Asp Arg Leu Leu
    370                 375                 380

Leu Phe Pro Phe Leu Ser Pro Gln Arg Asp Pro Glu Ile Tyr Thr Asp
385                 390                 395                 400

Pro Glu Val Phe Lys Tyr Asn Arg Phe Leu Asn Pro Asp Gly Ser Glu
                405                 410                 415

Lys Lys Asp Phe Tyr Lys Asp Gly Lys Arg Leu Lys Asn Tyr Asn Met
            420                 425                 430
```

```
Pro Trp Gly Ala Gly His Asn His Cys Leu Gly Arg Ser Tyr Ala Val
        435             440                 445

Asn Ser Ile Lys Gln Phe Val Phe Leu Val Leu Val His Leu Asp Leu
    450             455             460

Glu Leu Ile Asn Ala Asp Val Glu Ile Pro Glu Phe Asp Leu Ser Arg
465             470             475                 480

Tyr Gly Phe Gly Leu Met Gln Pro Glu His Asp Val Pro Val Arg Tyr
            485             490             495

Arg Ile Arg Pro
            500
```

COMPOSITIONS AND METHODS FOR ANGIOGENIC THERAPY UTILIZING GENES ENCODING ETS-1

CROSS REFERENCES TO RELATED APPLICATIONS

This application is a division of U.S. patent application Ser. No. 10/312,435, filed Apr. 28, 2003, now abandoned, which is a National Stage Entry of International Application Number PCT/JP01/05514, filed Jun. 27, 2001, which claims the benefit of Japanese Application Number 2000-388624, filed Dec. 21, 2000 and Japanese Application Number 2000-192480, filed Jun. 27, 2000, the disclosure of which is incorporated herein by reference in their entireties.

TECHNICAL FIELD

The present invention relates to novel pharmaceutical compositions for angiogenic therapy. More specifically, the present invention relates to novel pharmaceutical compositions for angiogenic therapy that contain, as the active ingredients, at least one substance selected from the group consisting of substances having vasodilating effect and/or platelet aggregation inhibitory effect and substances producing them. The present invention also relates to a gene encoding angiogenesis factor. In addition, a novel application of prostacyclin synthase gene and ets-1 gene for angiogenic therapy, etc.

BACKGROUND ART

Development of new blood vessels and angiogenesis are initiated along with activation of endothelial cells of parental blood vessels. Growth factors that have been shown, in addition to the stimulation of such angiogenesis in vivo, to function mitogenically toward endothelial cells in vitro are termed "angiogenesis factor (angiogenesis growth factor)".

The first therapeutic application of angiogenesis factor was reported by Folkman et al (N. Engl. J. Med. 285, 1182-1186 (1971)). According to later studies, the use of recombinant angiogenesis factors, such as the fibroblast growth factor (FGF) family (Science 257, 1401-1403 (1992); Nature 362, 844-846 (1993)), endothelial growth factor (EGF) (J. Surg. Res. 54, 575-583 (1993)), and vascular endothelial growth factor (VEGF), has been confirmed to promote and/or accelerate development of collateral circulatory tract in animal models of myocardial and hind limb ischemia (Circulation 90, II-228-II-234 (1994)). Furthermore, the present inventors discovered that hepatocyte growth factor (HGF), like VEGF, functions as an endothelium-specific growth factor (J. Hypertens. 14, 1067-1072 (1996)).

The strategy wherein angiogenesis factors are used for treating angiopathy (as mentioned above) is referred to as "angiogenic therapy." Recently, extremely active research on angiogenic therapy is in progress for ischemic diseases and arterial diseases using genes of above-mentioned angiogenesis factors.

For example, the present inventors have elucidated the effectiveness of HGF genes against arteriosclerosis obliterans (ASO) (Circulation 100, No. 18, No. 1672 (1999); Japanese Circulation Journal 64 (Suppl.I), 478, No. P079 (2000)). Furthermore, it has been revealed that the HGF gene effectively functions against ischemic-reperfusion injury in myocardial infarction (Circulation 96, No. 8, No. 3459 (1997); Ann. Thorac. Surg. 67, 1726-1731 (1999); Gene Therapy, 7, 417-427 (2000)).

Furthermore, the effectiveness of the VEGF gene on swine myocardial ischemia model (Human Gene Therapy 10, 2953 (1999)) and rabbit hind limb ischemia model (Circulation 96 (suppl II): II-382-388 (1997)) has been established. In addition, the effect of VEGF on ASO patients (Circulation 97, 1114-1123 (1998)) and angina pectoris patients (Ann. Thorac. Surg. 68, 830-837 (1999)) has also been reported. Currently, in the U.S., clinical studies of VEGF gene therapy for ASO patients and angina pectoris patients are being carried out by groups such as Isner et al.

Regarding the bFGF gene, it has been reported that the number of blood vessels increase due to intramuscular introduction of the bFGF gene into a mdx mouse, a model for muscular dystrophy (Gene Therapy 6(7), 1210-1221 (1999)).

Prostacyclin (prostaglandin $I_2$; $PGI_2$), a kind of prostaglandin, is an unstable lipid mediator having a half-life of 5 to 10 minutes (Arch. Gynecol. Obstet. 243, 187-190 (1988)) It elucidates a strong vasodilating effect and platelet aggregation inhibitory effect through an increase of the cAMP levels mediated via G protein-coupled receptor (N. Engl. J. Med. 17, 1142-1147 (1979)). Currently, vasodilators, such as the $PGI_2$, $PGE_1$ (prostaglandin $E_1$) and derivatives thereof (analogues), are widely used for the therapy of various types of angiopathy. Specifically, expecting functions, such as vasodilatation and platelet aggregation inhibition, intra-arterial injection and intravenous injection of the $PGE_1$ are performed against peripheral hematogenic disorders (e.g., ASO and TAO (thromboangiitis obliterans)). Such injections have become is an established therapeutic method. Furthermore, since the $PGI_2$ has a strong effect and its inactivation occurs rapidly, various derivatives (iloprost, beraprost sodium, etc.) have been developed. These derivatives are used for the therapy of peripheral vascular occlusive disease and chronic arterial occlusion (Prostaglandins, Leukotrienes and Essential Fatty Acids. 54, 327-333 (1996); Yakugaku Zasshi, 117, 509-521 (1997)). Furthermore, $PGE_1$ and $PGI_2$ are used against peripheral circulatory dysfunction due to collagen disease, Raynaud's phenomenon, maintenance of extracorporeal circulation (Minerva Med. 89, 405-409 (1998)), heart failure (Am. Heart J. 134, 44-54 (1997)), and so on.

As mentioned above, substances, such as $PGI_2$, that have vasodilating effect and platelet aggregation inhibitory effect are known to be effective against various types of angiopathies. However, these substances have never been used in combination in the aforementioned angiogenic therapy with the HGF gene, and it has not been determined as to what kind of effects can be expected by such combination.

Furthermore, angiogenesis factors, such as HGF, VEGF, bFGF, and EGF, are know to enhance the expression of ets-1 (erythroblastosis virus oncogene homolog 1), a transcription regulatory factor, and activate various types of factors involved in angiogenesis via the ets-1 (J. Cell. Physiol., 169, 522-531 (1996); "HGF no Bunshi Igaku (Molecular Medicine of HGF)", Medical Review, 179-185 (1998)) However, the ets-1 gene has never been used for angiogenic therapy and its effect completely unknown.

DISCLOSURE OF THE INVENTION

The objective of the present invention is to provide novel pharmaceutical compositions for angiogenic therapy. The object of the present invention is to provide novel pharmaceutical compositions for angiogenic therapy that contain, as the active ingredient, a gene encoding an angiogenesis factor and at least one substance selected from the group consisting of substances having vasodilating effect and/or platelet aggregation inhibitory effect and substances producing them. The present invention also relates to a novel application of prostacyclin synthase gene and ets-1 gene for angiogenic therapy, etc.

The present inventors examined the effect of the combined use of a gene of the PGI$_2$-synthesizing enzyme (PGI$_2$ synthase, hereinafter referred to as "PGIS") in angiogenic therapy along with the HGF gene. No drug indicating a satisfying effect by the combination in general angiogenic therapy using a gene of an angiogenesis factor has been found so far. Furthermore, effects of combined application with other genes have not been elucidated so far.

As a result of examination using a mouse hind limb ischemia ASO model, it has been revealed that the combined application of HGF gene or VEGF gene with PGIS gene show an unexpectedly remarkable improvement in hind limb blood flow, compared to the use of each of these genes alone. Furthermore, for the first time, the PGIS gene was found to reinforce the angiogenic effect of the HGF gene or VEGF gene, and to express an angiogenic effect even used alone.

According to the above-mentioned result, it was revealed that combined application of substances, such as PGT$_2$, or substances producing them (such as the PGIS gene), having vasodilating effect or platelet aggregation inhibitory effect is extremely effective in angiogenic therapy wherein a gene of an angiogenesis factor is used.

Furthermore, the present inventors examined the application of a gene encoding a transcription regulatory factor, ets-1, which is positioned downstream of HGF and VEGF in the signal transduction pathway, to angiogenic therapy. As a result, for the first time, administration of the ets-1 gene, a transcription regulatory factor, alone exhibited angiogenic effect. Furthermore, combined use of the ets-1 gene with the HGF gene was revealed to exhibit an even more remarkable angiogenic effect compared to the administrations of respective genes alone.

The present invention was accomplished based on the above-mentioned findings.

More specifically, the subjects of the present invention are:

(1) a pharmaceutical composition for angiogenic therapy which contains, as the active ingredients, at least one substance selected from the group of: substances having vasodilating effect and/or platelet aggregation inhibitory effect, and substances producing them; and a gene encoding an angiogenesis factor;

(2) a pharmaceutical composition for angiogenic therapy, which is characterized by the combined use of a gene encoding an angiogenesis factor with at least one substance selected from the group of: substances having vasodilating effect and/or platelet aggregation inhibitory effect, and substances producing them;

(3) a pharmaceutical composition for angiogenic therapy which contains, as the active ingredients, at least one substance selected from the group of: substances having vasodilating effect and platelet aggregation inhibitory effect, and substances producing them; and a gene encoding an angiogenesis factor;

(4) a pharmaceutical composition for angiogenic therapy, which is characterized by the combined use of a gene encoding an angiogenesis factor with at least one substance selected from the group of: substances having vasodilating effect and platelet aggregation inhibitory effect, and substances producing them;

(5) the pharmaceutical composition for angiogenic therapy of any one of (1) to (4), wherein the angiogenesis factor is HGF and/or VEGF;

(6) the pharmaceutical composition for angiogenic therapy of any one of (1) to (5), wherein the substances having vasodilating effect and/or platelet aggregation inhibitory effect and substances producing them are substances involved in the increase of cAMP;

(7) the pharmaceutical composition for angiogenic therapy of any one of (1) to (6), wherein the substance producing a substance having vasodilating effect and/or platelet aggregation inhibitory effect is in the form of a gene;

(8) the pharmaceutical composition for angiogenic therapy of (7), wherein the gene is prostacyclin synthase gene;

(9) a pharmaceutical composition for angiogenic therapy which contains HGF gene and prostacyclin synthase gene as the active ingredients;

(10) a pharmaceutical composition for angiogenic therapy which is characterized by the combined use of HGF gene and prostacyclin synthase gene;

(11) a pharmaceutical composition for angiogenic therapy which contains VEGF gene and prostacylin synthase gene as the active ingredients;

(12) a pharmaceutical composition for angiogenic therapy, which is characterized by the combined use of VEGF gene and prostacyclin synthase gene;

(13) the pharmaceutical composition for angiogenic therapy of any one of (1) to (12), wherein the composition is used for treating or preventing ischemic disease or arterial disease;

(14) the pharmaceutical composition for angiogenic therapy of (13) wherein the ischemic disease or arterial disease is selected from the group of arteriosclerosis obliterans, myocardial infarction, angina pectoris, cardiomyopathy, and cerebrovascular disease;

(15) the pharmaceutical composition for angiogenic therapy of any one of (1) to (14), wherein the gene is introduced in the form of naked DNA;

(16) an agent for potentiating the angiogenic effect due to a gene encoding an angiogenesis factor which contains, as the active ingredient, at least one substance selected from the group of: substances having vasodilating effect and/or platelet aggregation inhibitory effect, and substances producing them;

(17) an agent for potentiating the angiogenic effect due to a gene encoding an angiogenesis factor, which contains, as the active ingredient, at least one substance selected from the group of: substances having vasodilating effect and platelet aggregation inhibitory effect, and substances producing them;

(18) the agent for potentiating the angiogenic effect of (16) or (17) wherein the angiogenesis factor is HGF and/or VEGF;

(19) the agent for potentiating the angiogenic effect of any one of (16) to (18), wherein the substances having vasodilating effect and/or platelet aggregation inhibitory effect, and substances producing them are substances involved in the increase of cAMP;

(20) the agent for potentiating the angiogenic effect of any one of (16) to (19), which contains prostacyclin synthase gene as the active ingredient;

(21) an agent for potentiating the angiogenic effect due to HGF gene which contains prostacylin synthase gene as the active ingredient;

(22) the agent for potentiating the angiogenic effect of any one of (16) to (21), wherein the agent is used for treating or preventing ischemic disease or arterial disease;

(23) an angiogenic agent which contains prostacylin synthase gene as the active ingredient;

(24) the angiogenic agent of (23), wherein the agent is used for treating or preventing ischemic disease or arterial disease;

(25) a pharmaceutical composition for angiogenic therapy which contains ets-1 gene and another gene encoding an angiogenesis factor as the active ingredients;

(26) a pharmaceutical composition for angiogenic therapy, which is characterized by the combined use of ets-1 gene and another gene encoding an angiogenesis factor;

(27) the pharmaceutical composition for angiogenic therapy of (25) or (26), wherein the angiogenesis factor is HGF and/or VEGF;

(28) a pharmaceutical composition for angiogenic therapy which contains HGF gene and ets-1 gene as the active ingredients;

(29) a pharmaceutical composition for angiogenic therapy, which is characterized by the combined use of HGF gene and ets-1 gene;

(30) the pharmaceutical composition for angiogenic therapy of any one of (25) to (29), wherein the composition is used for treating or preventing ischemic disease or arterial disease;

(31) an agent containing ets-1 gene as the active ingredient that potentiates the angiogenic effect due to another gene encoding an angiogenesis factor;

(32) the agent for potentiating the angiogenic effect of (31), wherein the angiogenesis factor is HGF and/or VEGF;

(33) an agent for potentiating the angiogenic effect due to HGF gene, which contains ets-1 gene as the active ingredient;

(34) the agent for potentiating the angiogenic effect of any one of (31) to (33), wherein the agent is used for treating or preventing ischemic disease or arterial disease;

(35) an angiogenic agent which contains ets-1 gene as the active ingredient; and

(36) the angiogenic agent of (35) which is used for treating or preventing ischemic disease or arterial disease.

The present invention provides pharmaceutical compositions for angiogenic therapy that contain, as the active ingredients, at least one substance selected from the group consisting of substances having vasodilating effect and/or platelet aggregation inhibitory effect, and substances producing them; and a gene encoding an angiogenesis factor.

The phrase "gene encoding an angiogenesis factor," as employed herein for angiogenic therapy refers to a gene that encodes a protein or polypeptide that can induce the formation of new blood vessels or parts thereof. Specifically, they are exemplified by genes encoding HGF, VEGF, VEGF-2, acidic FGF (aFGF), basic FGF (bFGF), FGF-4, EGF, TGF-.alpha., TGF-.beta., platelet derived epithelial cell growth factor (PD-ECGF), platelet derived growth factor (PDGF), tumor necrosis factor-.alpha. (TNF-.alpha.), insulin-like growth factor, angiopoietin-1, and such. Furthermore, HIF-1 that regulates the expression of genes, such as VEGF, and genes that encode a transcription factor, such as members of the ets family including ets-1, are additional examples of such genes. Preferably, the genes are HGF gene and VEGF gene; the HGF gene being more preferable. The genetic sequences of these genes are registered in public databases and by utilizing these databases, one skilled in the art can readily clone the above-mentioned genes.

Hereinafter, the invention is explained using HGF gene and VEGF gene as the example.

In the present invention, the term "HGF gene," as employed herein refers to a gene that encodes HGF (HGF protein, as shown in SEQ ID NO:2). In addition, an HGF gene incorporated into an expression plasmid to be expressed may also be simply referred to as "HGF gene." Specifically, the gene includes cDNAs of HGF, such as those described in Nature, 342, 440 (1989) Examined Published Japanese Patent Application No. 2777678, Biochem. Biophys. Res. Commun., 163, 967 (1989) herein incorporated by reference, incorporated into an appropriate expression vector (non-virus vector, virus vector) such as those mentioned below. The nucleotide sequence of the cDNA (SEQ ID NO:1) encoding HGF (SEQ ID NO:2) is described in the aforementioned literature. In addition, it is also registered in databases such as Genbank. Thus, the cDNA of HGF can be cloned by performing a RT-PCR reaction, for example, on mRNAs derived from liver or leukocytes using appropriate DNA segments as PCR primers based on the sequence information. The cloning can be performed readily by one skilled in the art by referring to references, such as Molecular Cloning 2nd edition, Cold Spring Harbor Laboratory Press (1989).

The HGF gene of the present invention is not limited to those mentioned above. So long as the protein expressed from the gene substantially has the same angiogenic effect as HGF, the gene can be used as the HGF gene of the present invention. More specifically, the HGF gene of the present invention encompasses: 1) DNAs that hybridize under stringent conditions to the aforementioned cDNA; 2) DNAs encoding a protein consisting of the amino acid sequence of the protein encoded by the aforementioned cDNA, wherein one or more (preferably several) amino acids are substituted, deleted, and/or added; and such, so long as they encode a protein with angiogenic effect. The above DNAs of 1) and 2) can be readily obtained, for example, by site-directed mutagenesis method, PCR method, conventional hybridization methods, etc. Specifically, these methods can be performed by referring to the aforementioned reference, such as Molecular Cloning 2nd edition, Cold Spring Harbor Laboratory Press (1989).

The term "VEGF gene," as employed herein refers to a gene encoding VEGF protein. A VEGF gene incorporated into an expression plasmid to be expressed may also be simply referred to as the "VEGF gene." Specifically, such a gene is exemplified by a cDNA of a VEGF incorporated into an appropriate expression vector (non-virus vector, virus vector) such as those mentioned below. Regarding the VEGF genes in humans, the existence of four kinds of subtypes (VEGF121, VEGF165, VEGF189, and VEGF206) due to selective splicing during transcription have been reported (Science, 219, 983 (1983); J. Clin. Invest., 84, 1470 (1989); Biochem. Biophys. Res. Commun., 161, 851 (1989)) Any of these VEGF genes can be used in the present invention. However, VEGF165 gene is more preferable due to its strongest biological activity among the VEGF genes. Furthermore, like in the case of the aforementioned HGF, a gene of these VEGF, which is modified, is also included in the category of the VEGF gene of the present invention so long as the gene encodes a protein having an angiogenic effect.

Similar to the HGF gene, the VEGF gene can also be readily cloned by one skilled in the art based on the sequence described in the literature (for example, Science, 246, 1306 (1989)) and the sequence information registered in database; and modifications thereof can also be easily carried out.

Whether the above-mentioned HGF gene, VEGF gene, or genes encoding the modified forms of them possess angiogenic effect can be investigated, for example, via in vitro measuring the proliferative effect on vascular endothelial cells that is described in WO 97/07824. Alternatively, the angiogenic effect of the genes can be investigated via in vivo measuring the blood flow improving effect in a mouse hind limb ischemia model described in the Example, infra.

The above-mentioned genes encoding angiogenesis factors can be used alone or in combination in the angiogenic therapy of the present invention.

According to the Example mentioned below, for the first time it was revealed that the combined use of prostacyclin synthase gene (PGIS gene) in angiogenic therapy with HGF gene yields an unexpectedly remarkable effect. More specifically, it was demonstrated for the first time that a synergistic effect exceeding the sum of the effect of HGF gene alone and PGIS gene alone is achieved by the combination.

Herein, $PGI_2$ synthesized by PGIS has vasodilating effect, vascular permeability enhancing effect, and platelet aggregation inhibitory effect as mentioned above. Therefore, the reason for the aforementioned synergistic effect may be that the combined use of the HGF gene and PGIS gene provided an environment wherein the HGF can readily function at the ischemic site, i.e., an environment wherein angiogenesis by the HGF occurs easily through the effects, such as vasodilating effect and platelet aggregation inhibitory effect, possessed by $PGI_2$. As a result, this caused the aforementioned effect beyond expectation.

Therefore, substances having vasodilating effect and/or platelet aggregation inhibitory effect, or substances producing them are considered to cause an equivalent effect to the combined use of the PUTS gene. Thus, the present invention provides a pharmaceutical composition for angiogenic therapy that contains, as the active ingredient, at least one substance selected from the group consisting of substances having vasodilating effect and/or platelet aggregation inhibitory effect, and substances producing them and a gene encoding an angiogenesis factor.

Particularly, substances having both of the vasodilating effect and the platelet aggregation inhibitory effect, and substances producing them are preferably used in the angiogenic therapy of the present invention.

The phrase "substances having vasodilating effect," as employed herein includes all of the known substances having vasodilating effect (commercially available vasodilating agents, etc.), and may be any substance including, such as genes, proteins, and low molecular weight compounds. Specifically, the following substances can be presented as the examples.

Examples of general vasodilating agents (so called hypotensive agents) include: Ca antagonist, ACE inhibitor, .alpha.1 blocker, ANP (Atrial Natriuretic Peptide), potassium channel opener, hydrazine, and such.

Particularly, examples of vasodilating agents used for ASO include: prostaglandin preparations, such as $PGI_2$, $PGI_2$, and derivatives thereof (iloprost, beraprost sodium, $lipoPGE_1$, etc.); in addition, drugs that increase the concentration of NO donor or intracellular cGMP, such as nitrous acid compounds including nitroglycerin; and drugs that increase intracellular cAMP, such as, phosphodiesterase inhibitor.

Preferable agents are drugs that increase cAMP or prostaglandin preparations, more preferable are $PGI_2$, $PGI_2$, and derivatives thereof (analogues), and the $PGI_2$ derivatives are even more preferable. "Substances having platelet aggregation inhibitory effect" includes all of the known substances having platelet aggregation inhibitory effect (commercially available antiplatelet agents, etc.), and may be any substance, such as genes, proteins, and low-molecular weight compounds. Specifically, such substances are exemplified by the aforementioned prostaglandin preparations, such as $PGI_2$, $PGE_1$, and derivatives thereof (iloprost, beraprost sodium, $lipoPGE_1$, etc.), as well as arachidonic acid metabolic inhibitor, adenylcyclase activator, phosphodiesterase III inhibitor, $5-HT_2$ receptor antagonist, arachidonic acid metabolism inhibitor, and phosphodiesterase V inhibitor.

Preferable substances are drugs that increase cAMP, or prostaglandin preparations. More preferable are $PGI_2$, $PGE_1$, and stable derivatives thereof (analogues), and the $PGI_2$ derivatives are even more preferable.

The above term "substances that produce substances having vasodilating effect and/or platelet aggregation inhibitory effect" refers to substances that synthesize, produce, or induce the aforementioned substances having vasodilating effect and/or platelet aggregation inhibitory effect. Specifically, they indicate substances that synthesize, produce, or induce the aforementioned substances that increase prostaglandin or cAMP.

These substances may be genes, proteins, and low molecular weight compounds. However, for example, in the case of synthases that synthesize vasodilating substances and such, the substance is preferably used in the form of gene. Specific examples of the genes include: PGIS gene, cyclooxygenase-1 (COX-1) gene, cyclooxygenase-2 (COX-2) gene (Proc. Natl. Acad. Sci. USA, 89 (16), 7384-7388 (1992)), NO synthase (endothelial and inducible) gene, cytochrome P450 gene, ANP (Atrial Natriuretic Peptide) gene, BNP (Brain Natriuretic Peptide) gene, CNP (C-type Natriuretic Peptide) gene, and such. Preferable genes include the PGIS gene, COX-1 gene, and COX-2 gene, and the PGIS gene is more preferable. The genetic sequences of all of these genes are registered in public databases, and those skilled in the art can readily clone the genes using these registered genes.

An example wherein the PGIS gene is used is explained below.

Herein, the term "PGIS gene" refers to a gene that encodes a PGIS protein (as shown in SEQ ID NO:4). The PGIS gene incorporated into an expression plasmid so as to be expressed may also be simply referred to as the "PGIS gene". Specifically, a cDNA of PGIS (SEQ ID NO:3) described in BBRC 200(3), 1728-1734 (1994) herein incorporated by reference, and WO 95/30013 incorporated into an appropriate expression vector (non-virus vector, virus vector), such as those mentioned below, can be exemplified. Furthermore, similar to the aforementioned HGF gene and VEGF gene, a PUTS gene which is modified is also included in the category of the PGIS gene of the present invention so long as the gene encodes a protein having the effect as the PGIS.

As with the HGF gene and VEGF gene, the PGIS gene can also be cloned readily by one skilled in the art based on the sequence described in the aforementioned literature, or on the sequence information registered in the database. The PGIS gene can also be modified easily. Whether a protein encoded by the gene has the desired PGIS activity can be measured, for example, by enzyme immunoassay using 6-keto Prostaglandin F1 .alpha. enzyme immunoassay kit (Cayman, catalogue No. 190 515211), or by a method for detecting metabolites of the prostacyclin synthase by thin layer chromatography (TLC). Alternatively, the effect of enhancement of angiogenic effect due to an angiogenesis factor can be measured by measuring the effect of its combined use with an angiogenesis factor on a mouse hind limb ischemia model described below in the Example.

The above-mentioned substances that have vasodilating effect and/or platelet aggregation inhibitory effect, or substances producing them, alone or by combining some of these substance, can be used in angiogenic therapy using an angiogenesis factor gene is used.

Below appear the method for introduction, form of introduction, and amount of introduction of the pharmaceutical compositions for angiogenic therapy according to the present invention.

1) Use of a Substance Having Vasodilating Effect and/or Platelet Aggregation Inhibitory Effect or a Substance (Gene) Producing it, and a Gene Encoding an Angiogenesis Factor To use a gene encoding an angiogenesis factor and a gene, such as the aforementioned PGIS gene, in combination, i.e., a combined application of two or more genes, both genes need to take the form of an agent for gene therapy. Representative combinations include the combination of the HGF gene and PGIS gene, or the VEGF gene and PGIS gene.

The form of administration to administer the agent for gene therapy to a patient can be classified into two groups, one using a non-virus vector, and the other using a virus vector. The method of preparation and administration thereof are described in detail in experiment manuals (Jikken Tgaku (Experimental Medicine) Supplementary Volume, "Idenshichiryo no Kisogij yutsu (Fundamental Techniques for Gene Therapy)", Yodosha, 1996; Jikken Igaku (Experimental Medicine) Supplementary Volume, "Idenshidonyu & Hatsugenkaiseki Jikkenho (Experimental Methods for Gene Transfer & Expression Analysis)", Yodosha, 1997; "Idenshiechiryo Kaihatsu Kenkyu Handbook (Handbook of Gene Therapy Research and Development)", Nihon Idenshichiryo Gakkai (The Japan Society of Gene Therapy) Edition, NTS, 1999). Detailed explanations are given below.

A. Use of Non-Virus Vector

Using a recombinant expression vector, a conventional gene expression vector introduced with an object gene, the object gene can be introduced into cells and tissues by the following method.

Examples of methods of gene transfection into cells include: calcium phosphate co-precipitation method, method of direct infusion of DNA using a glass capillary tube, etc.

Examples of gene transfection into tissues include: the method of gene transfection by internal type liposome, method of gene transfection by electrostatic type liposome, HVJ (hemagglutinating virus of Japan)-liposome method, improved type HVJ-liposome method (HVJ-AVE liposome method), receptor-mediated method of gene transfection, method of importing a carrier (metal particles) along with a DNA molecule into cells by particle gun, method of direct introduction of naked-DNA, method for introduction by a positively charged polymer, and so on. The recombinant expression vector can be introduced into a cell using any of these methods. Among these methods, the method of direct introduction of naked-DNA is most convenient, and thus is a preferred method for introduction from that perspective. Alternatively, due to its extremely high fusion activity with the cell membrane compared to conventional liposome methods, the HVJ-liposome method is a preferred form for transfection. Although the Z strain (obtained from ATCC) is preferred as the HVJ, fundamentally, other HVJ strains (for example ATCCVR-907, ATCCVR-105, and such) can be also used.

Any expression vector can be used in the present invention so long as it can express the desired gene in vivo, and includes, for example, pCAGGS (Gene, 108, 193-200 (1991)), pBK-CMV, pcDNA3.1, pZeoSV (Invitrogen, Stratagene).

The two or more genes mentioned above can be transfected into the body simultaneously as a mixture of two or more recombinant expression vectors, which were prepared by incorporating the genes into discrete expression vectors, or separately with a time interval. Alternatively, a single expression vector wherein the two or more genes are incorporated into one expression vector, can be also introduced. Furthermore, with the aforementioned liposomal preparations, transfection can be carried out by enclosing two or more recombinant expression vectors into one liposome, or by enclosing each recombinant expression vector into separate liposomes.

B. Use of Virus Vector

Examples of virus vectors include recombinant adenovirus, retrovirus, etc. More specifically, a gene is introduced into a cell by introducing a desired gene into a DNA virus or RNA virus, such as avirulent retrovirus, adenovirus, adeno-associated virus, herpes virus, vaccinia virus, poxvirus, poliovirus, Sindbis virus, Sendai virus, SV40, and immunodeficiency virus (HIV); the recombinant virus is infected into the cell.

Among the aforementioned virus vectors, the infection efficiency of adenoviruses is known to be much higher than other virus vectors. Thus, from this perspective, the use of the adenovirus vector system is preferred.

Similar to the above-mentioned non-virus vector, these adenovirus vectors mentioned above can be introduced simultaneously as a mixture, or separately with a time interval by preparing recombinant expression vectors introduced with respective two or more genes. Alternatively, a single recombinant expression vector wherein two or more genes are incorporated into one expression vector can be introduced.

Furthermore, two or more genes can be introduced into the living body using both of the aforementioned techniques using non-virus vector and virus vector.

Methods for introducing the agent of the present invention for gene therapy include: (i) the in vivo method that introduces the agent for gene therapy directly into the body; and (ii) the ex vivo method that harvests a certain type of cell from the body, introduces the agent for gene therapy into the cell outside the body, and then returns the modified cell to the body (Nikkei Science, April 1994, 20-45; Gekkann Yakuji 36 (1), 23-48, 1994; Jikken Igaku (Experimental Medicine) Supplementary Volume, 12 (15), 1994; "Idenshi-chiryo Kaihatsu Kenkyu Handbook (Handbook of Gene Therapy Research and Development)", Nihon Idenshichiryo Gakkai (The Japan Society of Gene Therapy) Edition, NTS, 1999). The in vivo method is preferred in the present invention.

When administering by the in vivo method, administration is carried out via an appropriate administration route depending on the disease to be treated, target organ, and so on. For example, the administration can be intravenous, intra-arterial, subcutaneous, intradermal, intramuscular, etc., or via direct local administration to the lesion itself.

Various formulations (for example, liquid preparations, etc.) suitable for each of the above-mentioned forms of administration may be adopted as the form of the preparation. For example, to prepare an injection containing a gene as the active ingredient, the injection can be prepared by conventional methods, for example, by dissolving in an appropriate solvent (buffer solution, such as PBS, physiological saline, sterilized water, etc.); sterilizing by filtration through a filter as necessary, and then loading into a sterile container. A conventional carrier and such may be added as required to the injection. Alternatively, a liposome, such as HVJ-liposome, can be in the form of liposome preparations, such as suspension, frozen agent, or centrifugally concentrated frozen agent.

Furthermore, to facilitate the presence of the genes around the diseased site, a controlled release preparation (miniature pellet preparation, etc.) can be prepared and implanted near the affected area. Alternatively, continuous and gradual administration to the affected area using an osmotic pump is available.

The aforementioned two or more recombinant expression vectors may take different formulations, or it may be a formulation of a mixed combined agent.

The amount of the genes contained in the preparation can be adjusted appropriately depending on the disease to be treated, age and weight of the patient, etc.; however, generally it is preferred that 0.0001 to 100 mg, or preferably 0.001 to 10 mg of each gene is administered once every few days or every few months.

2) Use of Substances Having Vasodilating Effect and/or Platelet Aggregation Inhibitory Effect, and Substances (Low Molecular Weight Compounds, Proteins, Etc.) Producing Them; and a Gene Encoding an Angiogenesis Factor When a gene encoding an angiogenesis factor and a low molecular weight compound, protein, peptide, etc. are used in combination, the gene encoding the angiogenesis factor should be in the form of the aforementioned agent for gene therapy. On the other hand, low molecular weight compounds and such are administered orally or parenterally in a conventional form of a pharmaceutical composition. Representative combinations include the combination of the HGF gene and PGI.sub2 derivative, the VEGF gene and PGT.sub2 derivative, and so on.

Explanation on pharmaceutical compositions containing the aforementioned low molecular weight compound, protein, and so on as the active ingredient are described in the following.

The administration method, dose, etc. of the aforementioned low molecular weight compounds or proteins that are already commercially available as vasodilating agents or platelet aggregation inhibitory agents (antiplatelet agents) can be set according to the statement of virtues. However, in general, examples of the form of administration and method of administration are the following.

For oral administration, it can be administered in an administration form conventionally used in the art. For parenteral administration, it can be administered in administration forms such as local administration agent (transdermal agent, etc.), rectal administration agent, injection, and nasal agent.

Examples of oral agents or rectal administration agents include capsules, tablets, pills, powders, drops, suppositories, liquid preparations, etc. Examples of injections include sterile solutions, suspensions, emulsions, and such; and specifically, water, water-propylene glycol solution, buffering solution, 0.4% physiological saline, and such can be presented as examples. Local administration agents include, for example, cream, ointment, lotion, transdermal agents, and such.

The above-mentioned dosage forms are formulated with pharmaceutically acceptable fillers and additives by methods conventionally performed in the art. Pharmaceutically acceptable fillers and additives include carriers, binders, perfume, buffers, thickeners, coloring agents, stabilizers, emulsifiers, dispersants, suspending agents, preservatives, pH regulating agents, tonicity regulating agents, lubricants, and such. Pharmaceutically acceptable carriers include, for example, magnesium carbonate, lactose, pectin, starch, methyl cellulose, and such.

Such pharmaceutical compositions can be administered via an appropriate administration route depending on the disease to be treated, target organ, and such. For example, the administration can be intravenous, intra-arterial, subcutaneous, intradermal, intramuscular, etc., or direct local administration to the lesion itself. Furthermore, oral administration and administration as a suppository are also possible.

The dose and frequency of administrations vary depending on the symptom, age, weight of the patient, administration form, and such; but it is normally within the range of approximately 0.0001 to approximately 500 mg, preferably within the range of approximately 0.001 to approximately 100 mg for adults per day, which is administered at a time or divided for several administrations.

Pharmaceutical compositions that contain the above-mentioned low molecular weight compounds and proteins as the active ingredients can be administered simultaneously with the agent for gene therapy containing a gene encoding an angiogenesis factor, or they can be administered separately with a time interval.

The pharmaceutical compositions for angiogenic therapy of the present invention that have been described so far can be applied to all diseases that require angiogenic therapy. Specifically, ischemic disease or arterial disease can be exemplified as such diseases. More specifically, examples of heart diseases include ischemic heart disease, myocardial infarction, acute myocardial infarction, myocardosis, angina pectoris, unstable angina, coronary arteriosclerosis, heart failure, and such; and examples of ischemic diseases of the extremities include arteriosclerosis obliterans (ASO), Berger's disease, vascular injury, arterial embolism, arterial thrombosis, arterial occlusion of the organ, aneurysm, and such. Other examples are cerebrovascular diseases. Specifically, examples of cerebrovascular diseases include cerebrovascular occlusion, cerebral infarction, cerebral thrombosis, cerebral embolism, stroke, cerebral hemorrhage, moyamoya disease, cerebrovascular dementia, Alzheimer type dementia, sequela of cerebral hemorrhage, and sequela of cerebral infarction. Among these diseases, the pharmaceutical compositions of the present invention are effectively used particularly against arteriosclerosis obliterans.

Furthermore, the present invention also provides an agent for potentiating the angiogenic effect due to a gene encoding an angiogenesis factor which contains, as the active ingredient, at least one substance selected from the group consisting of substances having vasodilating effect and/or platelet aggregation inhibitory effect, and substances producing them. As mentioned above, the aforementioned substance that is the active ingredient of the pharmaceutical composition for angiogenic therapy of the present invention has the effect of enhancing the angiogenic effect due to a gene encoding an angiogenesis factor. Therefore, as mentioned above, it can be used as one of the components of a pharmaceutical composition for angiogenic therapy, or alternatively, it can be used alone as a potentiating agent to increase the angiogenic effect due to a gene encoding an angiogenesis factor. The potentiating agent of the present invention is used effectively in cases where the effect of the gene encoding the angiogenesis factor is insufficient. The potentiating agent of the present invention may comprise only one component (substance), or pulural components (substances) in combination.

Specifically, the active ingredients of the potentiating agents of the present invention include the aforementioned PGIS gene or COX gene. Further examples are PGI.sub2, PGE1, their derivatives, and such; and is preferably the PGIS gene. The angiogenesis factor may be HGF or VEGF as mentioned above.

The administration method, administration form, accommodated disease, and such of the potentiating agent of the present invention are the same as those of the aforementioned pharmaceutical compositions for angiogenic therapy.

Furthermore, the present invention provides angiogenic agents which contain the PGIS gene as the active ingredient. That is, for the first time, the administration of the PGIS gene was revealed to cause angiogenic effect independently. This is a novel effect which had been unknown, and due to the finding the PGIS gene was found to be useable as an angiogenic agent. The angiogenic agent of the present invention can be used for all diseases (ischemic diseases, and arterial diseases) that require angiogenesis as those mentioned above. Moreover, administration method, administration form, and such are the same as those of the aforementioned pharmaceutical compositions for angiogenic therapy.

Furthermore, for the first time, ets-1 gene was revealed to be effective as a gene therapy agent for angiogenic therapy by the present invention. That is, as demonstrated below in the Examples, an angiogenic effect was observed by the independent administration of the ets-1 gene, and that combined use of the ets-1 gene with HGF gene was revealed to enhance angiogenesis more compared to independent administration of each of them.

Herein, ets-1 is a transcription regulatory factor whose expression is commonly enhanced by the action of angiogenesis factors such as HGF, VEGF, bFGF, and EGF. These angiogenesis factors are known to activate various factors involved in angiogenesis via the ets-1 (J. Cell. Physiol., 169, 522-531 (1996); "HGF no Bunshi Igaku (Molecular Medicine of HGF)", Medical Review, 179-185 (1998))). Therefore, the same effect as the combined use of HGF gene can be expected by the combined use of angiogenesis factor genes other than the HGF gene, such as VEGF gene, with the ets-1 gene.

Thus, the present invention provides novel pharmaceutical compositions for angiogenic therapy wherein the ets-1 gene is used alone or subjected to a combined application with other angiogenesis factors. Specifically, the following three examples can be presented:

(1) a pharmaceutical composition for angiogenic therapy, which contains, as the active ingredients, ets-1 gene and another gene encoding an angiogenesis factor;

(2) an agent that contains ets-1 gene as the active ingredient for potentiating the angiogenic effect due to another gene encoding an angiogenesis factor; and (3) an angiogenic agent that contains ets-1 gene as the active ingredient.

Herein, the term "ets-1 gene" refers to a gene encoding an ets-1 (ets-1 protein). Furthermore, an ets-1 gene incorporated into an expression plasmid so as to be expressed may also be simply referred to as the "ets-1 gene". Specifically, a cDNA of human ets-1, registered in GenBank as Acc. No. J04101, and described in Proc. Natl. Acad. Sci. U.S.A., 85 (21), 7862-7866 (1988), incorporated into an appropriate expression vector (non-virus vector, virus vector) for gene therapy, such as those mentioned above, can be exemplified. The ets-1 gene can be cloned, by methods similar to those mentioned above for the HGF gene and VEGF gene. Furthermore, the ets-1 gene of the present invention is not limited to a naturally occurring type, and includes genes SQ long as they express a protein that substantially has the same effect as the ets-1.

Such ets-1 genes are formulated into agents for gene therapy similarly to the aforementioned HGF gene and PGIS gene. Furthermore, method of introduction and amount of introduction into a living body, formulation, etc. thereof are the same as those mentioned for the HGF gene and PGIS gene.

As in above (1), for combined application of ets-1 gene with other genes (other than ets-1) encoding an angiogenesis factor, these two or more genes are formulated as follows. When using a non-virus vector, individual recombinant expression vectors constructed by incorporation of the genes into separate expression vectors are transfected into a living body simultaneously as a mixture, or separately with a time interval. Alternatively, a single expression vector wherein the two or more genes are incorporated into one expression vector can be also introduced. Alternatively, when the administration form is a liposomal preparation, the aforementioned individual recombinant expression vectors can be introduced by enclosing them into one liposome, or by enclosing the individual recombinant expression vectors into separate liposomes.

On the other hand, when using a virus vector, recombinant expression vectors wherein the two or more genes are incorporated into separate expression vectors can be introduced simultaneously as a mixture or separately with a time interval in a similar manner to the aforementioned non-virus vector. Alternatively, a single recombinant expression vector wherein the two or more genes are incorporated in one expression vector can be introduced.

Alternatively, both of the aforementioned non-virus vector and virus vector can be used to introduce the two or more genes into a living body.

A gene of an angiogenesis factor that is used in combination with the ets-1 gene may be any gene so long as the gene encodes a protein or polypeptide that can induce the formation of new blood vessels, or a portion thereof, as mentioned above. Preferable examples are the HGF gene and VEGF gene, and the HGF gene is more preferable.

Furthermore, as mentioned above in (2), the ets-1 gene of the present invention can be used alone as a potentiating agent for enhancing the angiogenic effect due to a gene encoding an angiogenesis factor, such as HGF and VEGF. Such a potentiating agent that contains the ets-1 gene as the active ingredient is effectively used when the effect of the gene encoding the angiogenesis factor is insufficient. In particular, it is effectively used as a potentiating agent for enhancing the effect of the HGF gene. Furthermore, the ets-1 gene of the present invention can be used alone as an angiogenic agent as mentioned above in (3). When using the ets-1 gene alone in this manner, the same administration method and administration form as mentioned above for agents for gene therapy are applied.

The above-mentioned angiogenic therapy using the ets-1 gene is applied, for example, to diseases, specifically, ischemic diseases or arterial diseases, more specifically, heart diseases, such as ischemic heart disease, myocardial infarction, acute myocardial infarction, myocardosis, angina pectoris, unstable angina, coronary arteriosclerosis, heart failure, and ischemic diseases of the extremities such as arteriosclerosis obliterans (ASO), Berger's disease, vascular injury, arterial embolism, arterial thrombosis, arterial occlusion of the organ, aneurysm. Other examples are cerebrovascular diseases and such. Specifically, examples of cerebrovascular diseases include cerebrovascular occlusion, cerebral infarction, cerebral thrombosis, cerebral embolism, stroke, cerebral hemorrhage, moyamoya disease, cerebrovascular dementia, dementia of the Alzheimer type, sequela of cerebral hemorrhage, and sequela of cerebral infarction. Among these diseases, the pharmaceutical compositions of the present invention containing the ets-1 gene as the active ingredient are used effectively, particularly against arteriosclerosis obliterans.

BEST MODE FOR CARRYING OUT THE INVENTION

Herein below, the present invention will be described using Examples, however, it is not to be construed as being limited thereto.

Example 1

Effect of Administration of HGF Gene, or PGIS Gene to Mouse Hind Limb Ischemia ASO Model (1) Materials The cDNA of human HGF (described in Unexamined Published Japanese Patent Application No. (JP-A) Hei 5-111383 herein incorporated by reference in its entirety) was cloned by a conventional method, and was inserted into an expression plasmid pcDNA3.1 (+) (Invitrogen) containing a cytomegalovirus (CMV) promoter to be used as human HGF gene.

The cDNA of human PGIS (B.B.R.C., Vol. 200, No. 3, p 1728-1734 (1994) herein incorporated by reference in its entirety) was cloned by a conventional method, and was inserted into an expression plasmid pCAGGS (Gene 108, 193-200 (1991)) containing a CMV enhancer and a .beta.-actin promoter to be used as human PGIS gene.

(2) Methods

C57BL/6J mouse (8 weeks old, male) was used. The mouse was anesthetized by intraperitoneal injection of 200 .mu.l of 10-fold diluted Nembutal, and further by ether inhalation when supplementation was necessary. Then, the arteriovenous of the left hind limb was tied up to produce a mouse hind limb ischemia ASO model. Ten days later, the blood flow in both hind limbs was evaluated using Laser Doppler Imager (LDI, Moor Instruments Ltd., MLDI5070), and the left-right ratio was calculated. After the evaluation, 500 .mu.g each of the genes of above (1) was administered into the left hind limb muscle in the form of naked plasmids. Four groups were set up: i.e., a control group without administration; a group given the HGF gene alone; a group given the PGIS gene alone; and a group given a combined application of the HGF gene and PGIS gene. 2 weeks and 4 weeks after the administration of the genes, the blood flow was evaluated using LDI, and the ratio was calculated. Furthermore, 4 weeks later, the left hind limb muscle was extirpated, and after preparing a frozen section, the capillary density in the muscle was measured by alkaline phosphatase staining. Significant difference test was performed by the Fisher's PLSD method.

(3) Result

Figure 1:
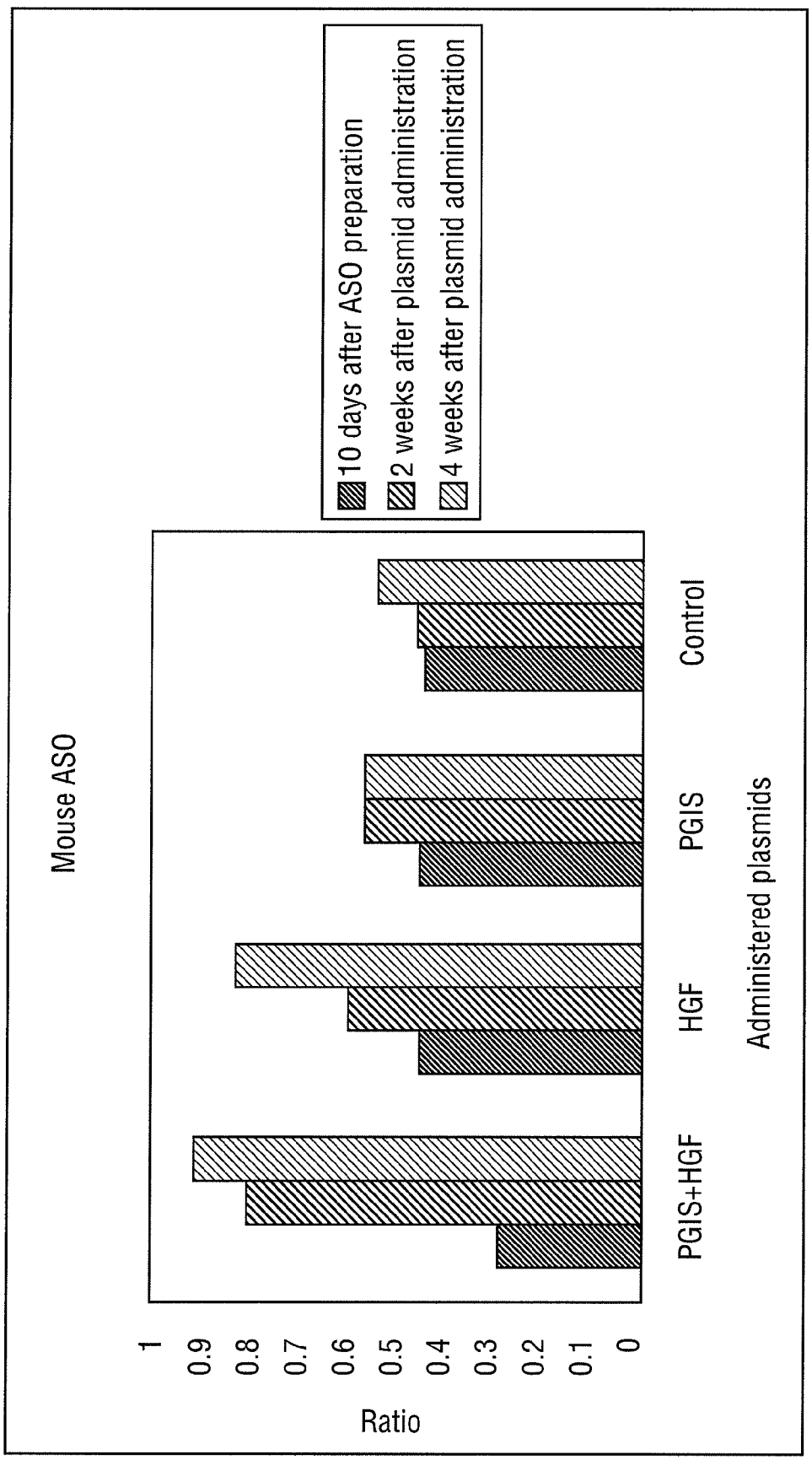
FIG. 1 is a graph showing the result of examination wherein the changes in the left-right ratios with time were investigated by measuring the hind limb blood flow using Laser Doppler Imager after the administration of the respective genes (control, HGF gene, PGIS gene, HGF gene+PGIS gene) to a mouse hind limb ischemia ASO model.
Figure 2:
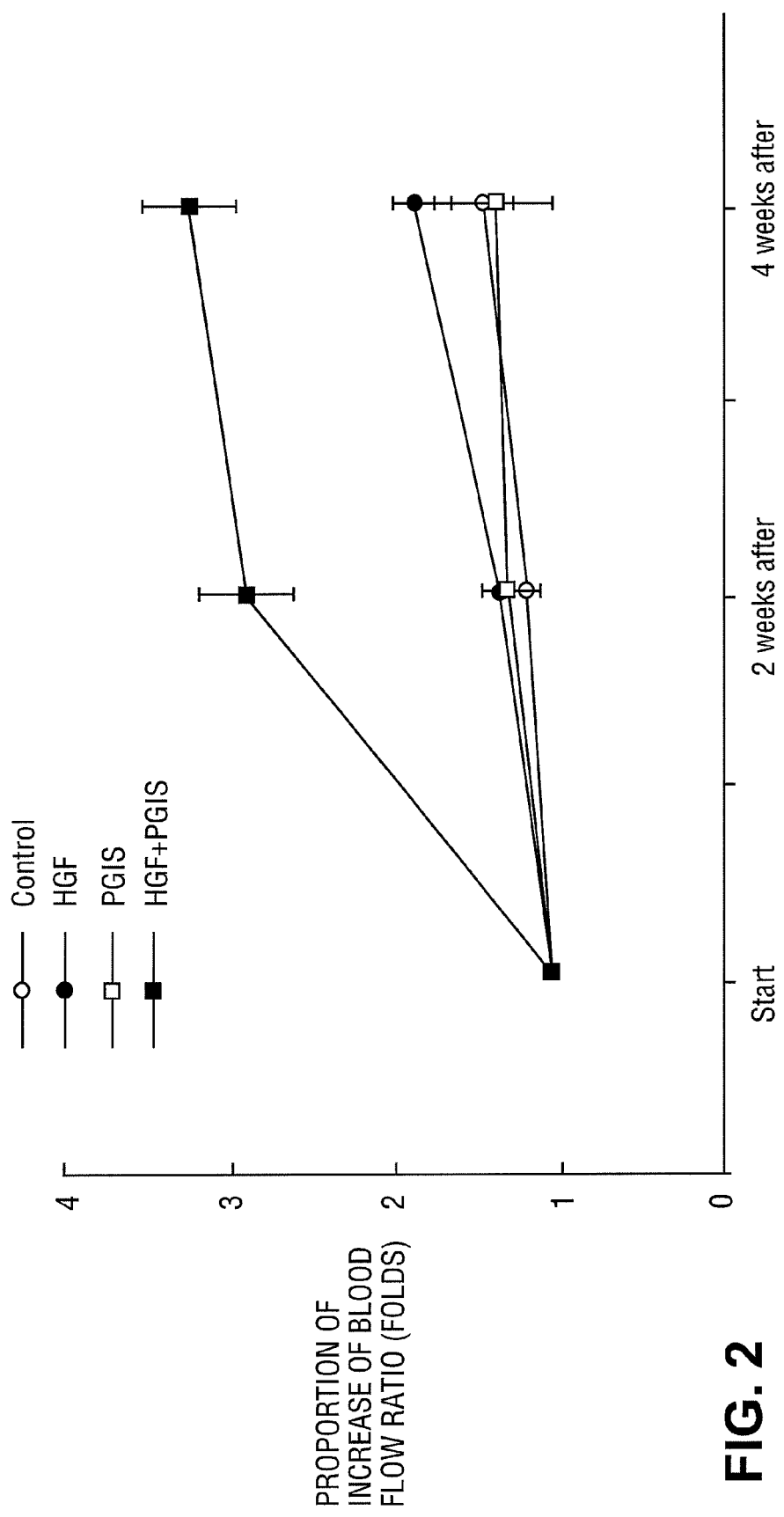
FIG. 2 is a graph showing the result of examination wherein the proportion of increase with time of the left-right ratio compared to that before the administration of the genes was investigated by measuring the hind limb blood flow using Laser Doppler Imager after the administration of the respective genes (control, HGF gene, PGIS gene, HGF gene+PGIS gene) to a mouse hind limb ischemia ASO model.

The changes in the ratio of the left-right hind limb blood flow with time was measured by LDI, and is shown in FIG. 1. Furthermore, the proportion of increase compared to the LDI ratio before the administration of the genes is indicated in FIG. 2. The blood flow was improved 2 weeks after the administration of the PGIS gene, but 4 weeks after the administration, it was nearly the same as that of the control group. By administering the HGF gene, the blood flow was improved both at 2 and at 4 weeks after administration. Furthermore, unexpectedly, the combined application of the PGIS gene and HGF gene remarkably improved the blood flow compared to independent administration of the genes (2 weeks later: control: 100%, HGF gene administration: 132%, PGIS gene administration: 125%, HGF gene+PGIS gene administration: 177%, P<0.01; 4 weeks later: control: 100%, HGF gene administration: 150%, PGIS gene administration: 104%, HGF gene+PGIS gene administration: 166%, P<0.01).

Figure 3:
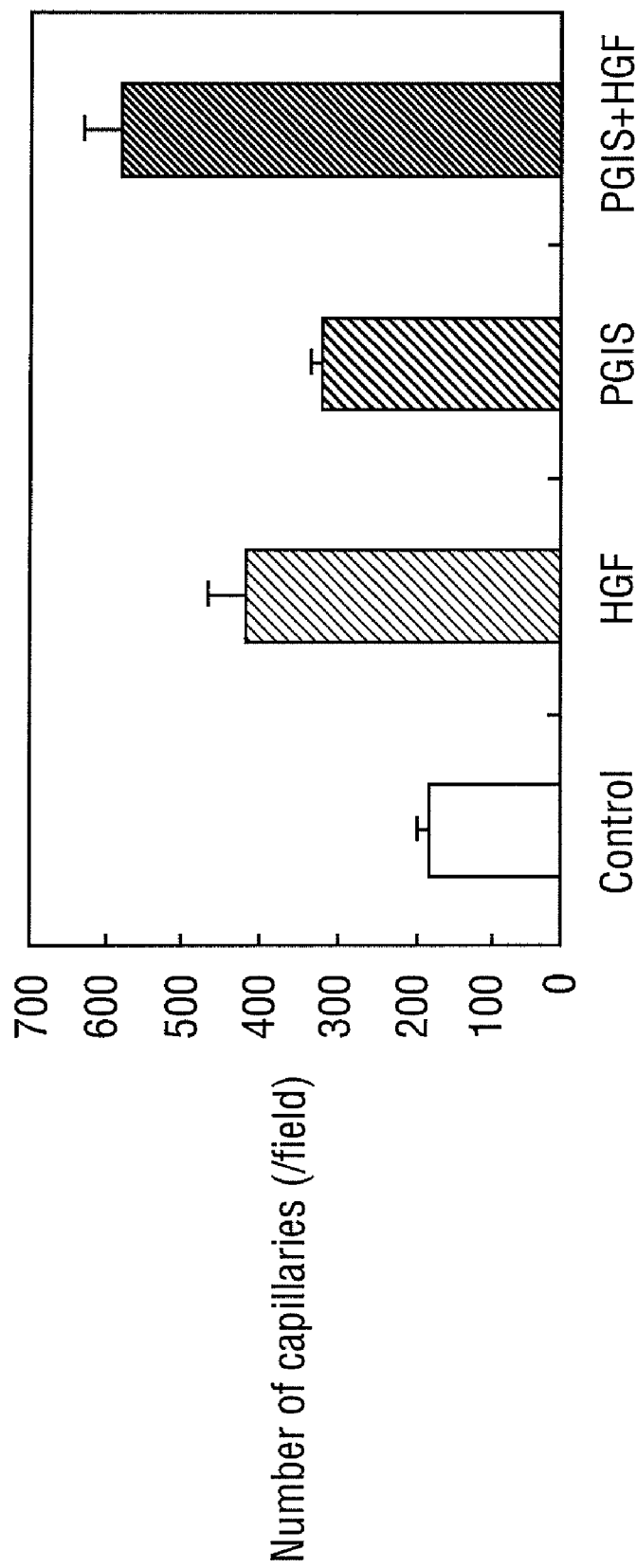
FIG. 3 is a graph showing the result of examination wherein the number of capillaries in the ischemic limb muscle were investigated after the administration of the respective genes (control, HGF gene, PGIS gene, HGF gene+PGIS gene) to a mouse hind limb ischemia ASO model.

The capillary densities in the muscles 4 weeks after the gene administration are shown in FIG. 3. The capillary density increased due to the administration of the PGIS gene or HGF gene. Furthermore, by the combined application of the PGIS gene and HGF gene, the capillary density increased remarkably compared to independent administration.

Example 2

Effect of Administration of HGF Gene, and Ets-1 Gene to Rat Hind Limb Ischemia ASO Model (1) Materials An expression plasmid carrying the human HGF gene, which is the same as that of Example 1, was used. The cDNA of human ets-1 (GenBank Acc. No. J04101, Proc. Natl. Acad. Sci. U.S.A., 85 (21), 7862-7866 (1988)) was cloned by a conventional method, and was inserted into a commercially available expression vector to be used as human ets-1 gene.

(2) Methods

Sprauge Dawley rats (12 weeks old, male) were used. The femoral artery from one side was extirpated to produce a rat hind limb ischemia ASO model. One week later, 100 .mu.g each of the genes was administered into the left hind limb muscle using the HVJ-liposome method. Four groups were set up: a control group wherein the vector was administered alone; a group given the HGF gene alone; a group given the ets-1 gene alone; and a group wherein the HGF gene and ets-1 gene were used in combination. Using Laser Doppler Imager (LDI) before gene administration and 4 weeks after gene administration, the blood flow in both hind limbs was evaluated, and the proportion of increase in the left-right blood flow ratio was calculated. Furthermore, the left hind limb muscle was extirpated, and after preparing a frozen section, the capillary density in the muscle was measured by alkaline phosphatase staining. To investigate the influence of the gene administration on the expression of endogenous HGF, intramuscular rat HGF concentration in the ischemic limb was measured using ELISA kit (Institute of Immunology).

(3) Result

By the independent administration of the ets-1 gene, the ets-1 binding activity in the muscular tissue increased. Furthermore, by the administration of the ets-1 gene, the proportion of increase of hind limb blood flow ratio measured using LDI rose (FIG. 4), and the capillary density in the muscle increased (FIG. 5), which results indicate the effect of angiogenesis, and effectiveness towards the ASO model due to the independent administration of the ets-1 gene. Furthermore, the intramuscular HGF concentration in the ischemic limb increased in the group that were given the ets-1 gene alone (FIG. 6 and FIG. 7), and this was considered to be one of the mechanisms of the effect of the ets-1 gene administration.

Figure 4:
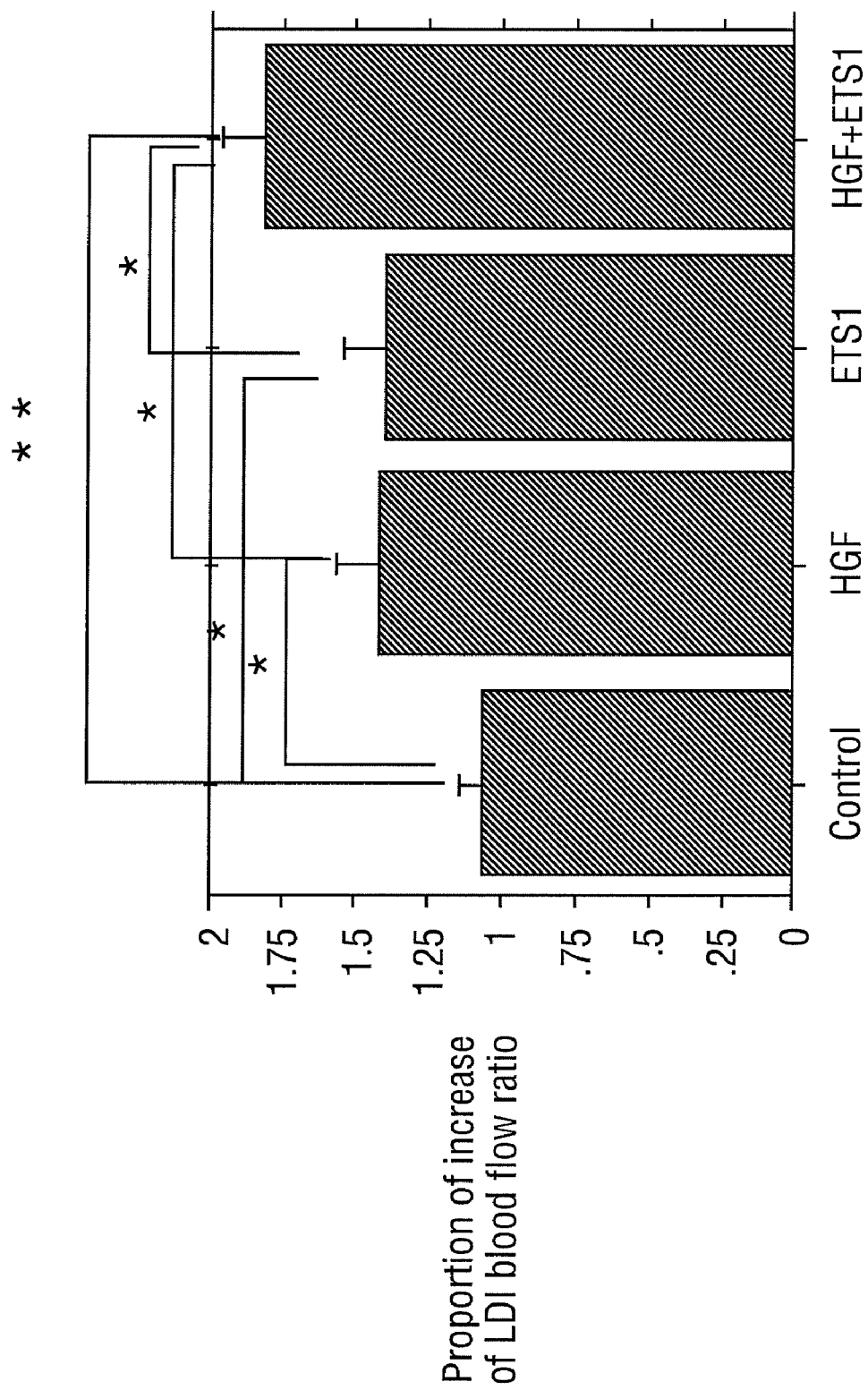
FIG. 4 is a graph showing the result of examination wherein the proportion of increase of the right-left hind limb blood flow ratio was investigated by measuring the hind limb blood flow using Laser Doppler Imager after the administration of the respective genes (control, HGF gene, ets-1 gene, HGF gene+ets-1 gene) to a rat hind limb ischemia ASO model.
Figure 5:
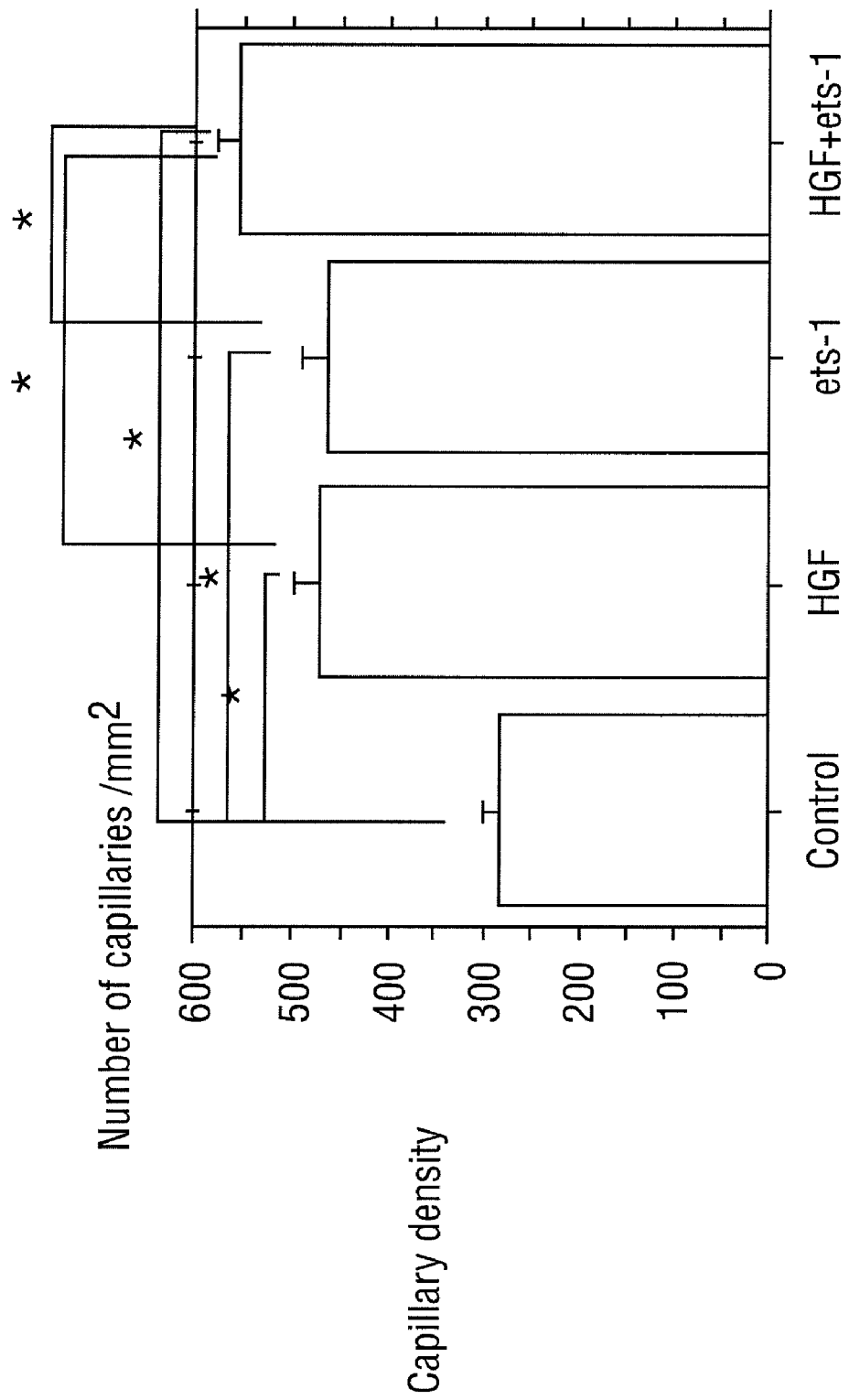
FIG. 5 is a graph showing the result of examination wherein the capillary density in the ischemic limb muscle was measured after the administration of the respective genes (control, HGF gene, ets-1 gene, HGF gene+ets-1 gene) to a rat hind limb ischemia ASO model.

In the group wherein the ets-1 gene and HGF gene was administered in combination, the proportion of increase of LDI blood flow ratio rose remarkably compared to the groups given ets-1 gene alone or HGF gene alone (FIG. 4). The intramuscular capillary density also increased significantly by the combined administration (FIG. 5). Therefore, gene transfection of both genes in combination was revealed to enhance angiogenesis more than when genes are used separately. Thus, the combination of the genes was more effective against ASO compared to the independent gene transfection.

Figure 6:
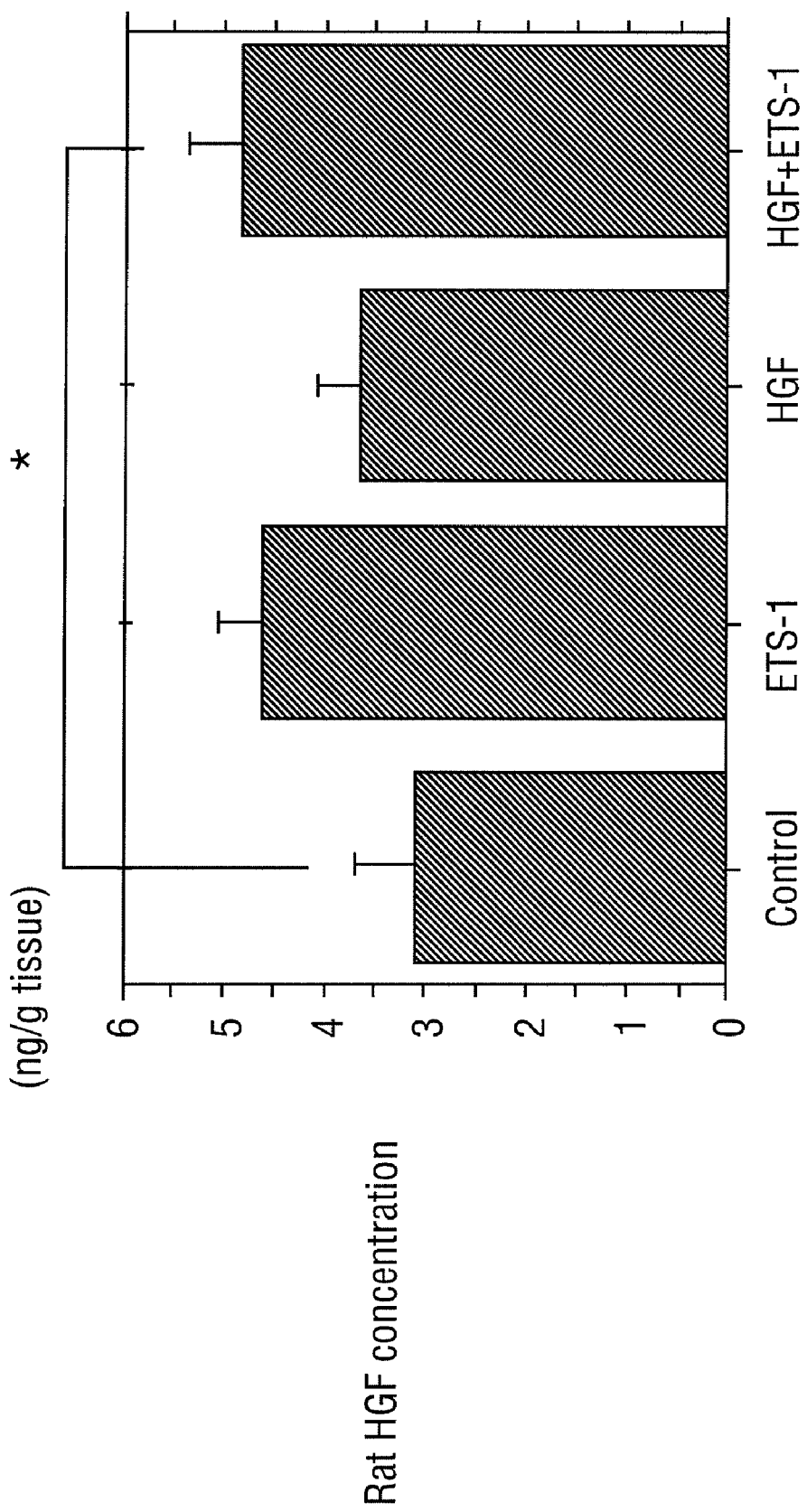
FIG. 6 is a graph showing the result of examination wherein the rat HGF concentration in the ischemic limb muscle was investigated after the administration of the respective genes (control, HGF gene, ets-1 gene, HGF gene+ets-1 gene) to a rat hind limb ischemia ASO model.
Figure 7:
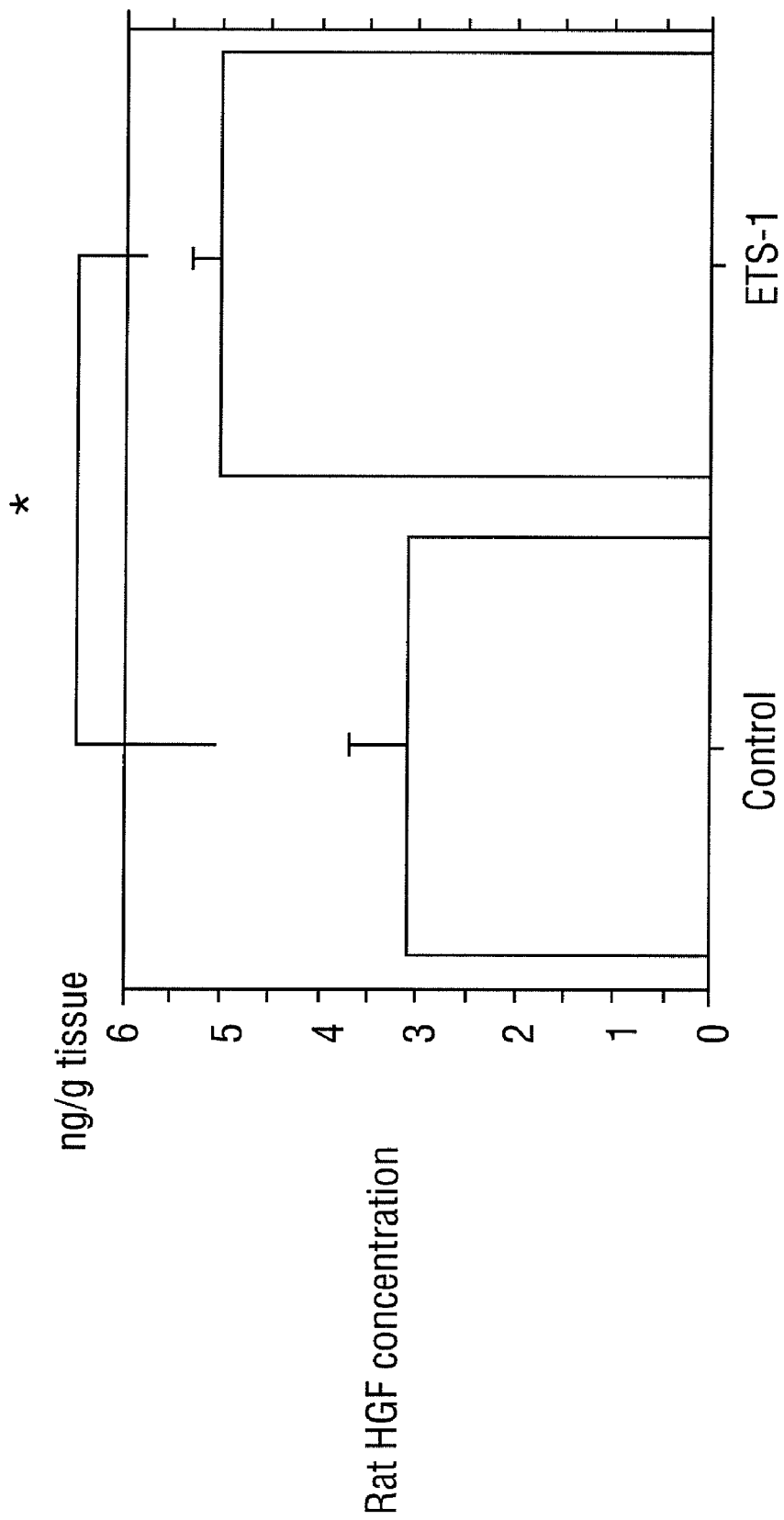
FIG. 7 is a graph showing the result of examination wherein the rat HGF concentration in the ischemic limb muscle was investigated after the administration of the ets-1 gene to a rat hind limb ischemia ASO model.

According to the measurement of the intramuscular endogenous HGF concentrations in rat ischemic limbs, the rat HGF concentration was higher in the group wherein the HGF gene and ets-1 gene was used in combination compared to the group given HGF gene alone (FIG. 6). The HGF was suggested to have an auto-loop type regulatory mechanism through the activation of ets-1 because the expression of the internal HGF was enhanced much more with the combined administration of the ets-1 gene than the administration of the HGF gene alone.

Example 3

Effect of Administration of VEGF Gene, and PGIS Gene to Mouse Hind Limb Ischemia ASO Model (1) Materials The cDNA of human VEGF165 (gift from Prof. Yonemitsu at Kyushu University Department of Surgery II) was cloned by a conventional method, and was inserted into the EcoRI site of expression plasmid pCAGGS (Gene 108, 193-200 (1991)) having a CMV enhancer and a .beta.-actin promoter to be used as human VEGF gene.

The cDNA of human PGIS (B.B.R.C., Vol. 200, No. 3, p 1728-1734 (1994)), was cloned by a conventional method, and was inserted into an expression plasmid pCAGGS (Gene 108, 193-200 (1991)) having a CMV enhancer and a .beta.-actin promoter to be used as human PGIS gene.

(2) Method

Figure 8:
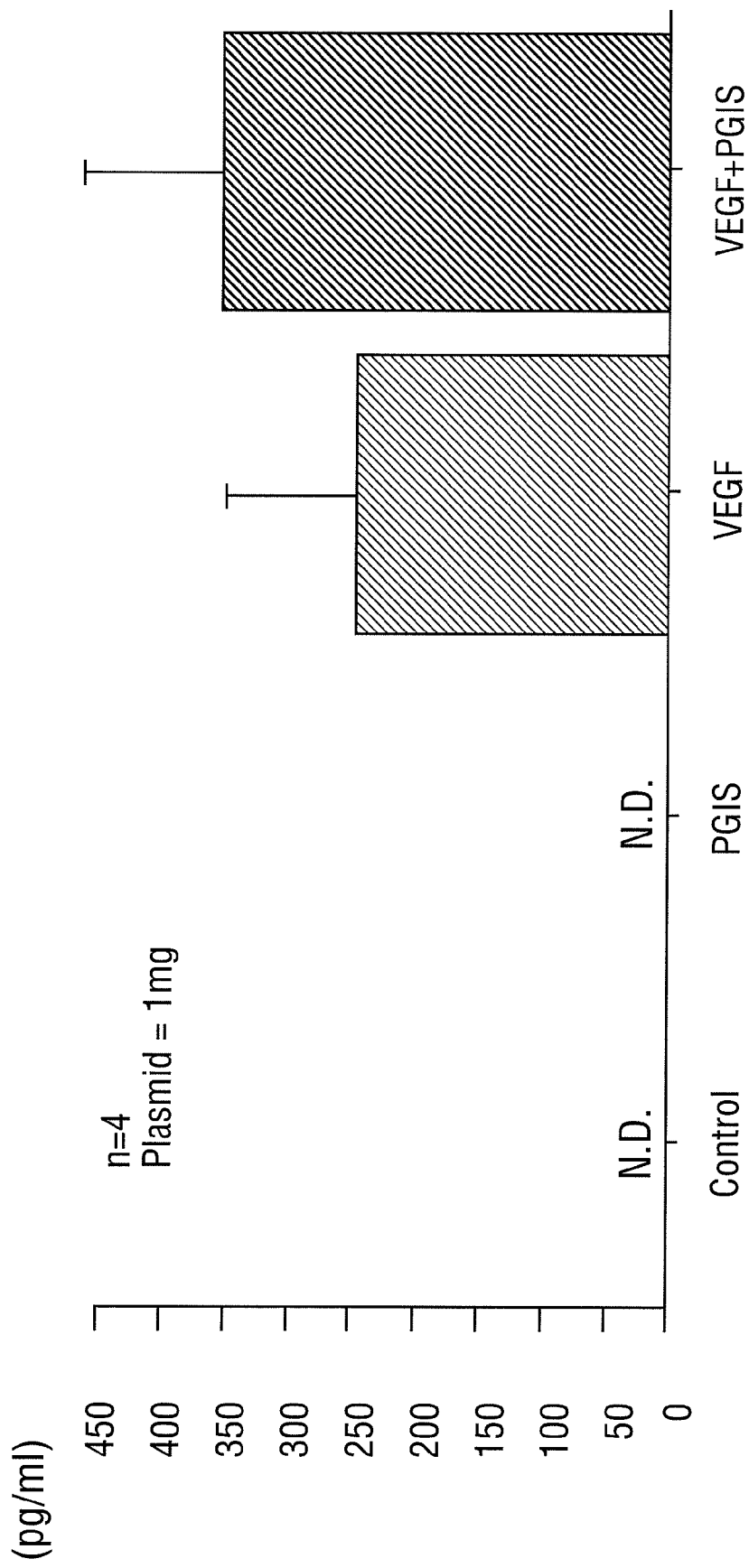
FIG. 8 is a graph showing the result of examination wherein the human VEGF concentration in the ischemic limb muscle was investigated after the administration of the PGIS gene, VEGF gene, or VEGF gene and PGIS gene to a mouse hind limb ischemia ASO model.

1. C57BL/6J mouse (8 weeks old, male) was used. The mouse was anesthetized by intraperitoneal injection of 200 .mu.l of 10-fold diluted Nembutal, and further by ether inhalation when supplementation was necessary. Then, the arteriovenous of the left hind limb was tied up to produce a mouse hind limb ischemia ASO model. After evaluation, 1 mg each of the above-mentioned genes of (1) was administered into the left hind limb muscle in the form of naked plasmids. Four groups were set up: a control group without administration; a group given the VEGF gene alone; a group given the PGIS gene alone; and a group given a combined application of the VEGF gene and PGIS gene. Four animals were included in each group. On the 5th day after the administration of each plasmid to the left tibialis muscle, the intramuscular concentration of human VEGF protein in the ischemic hind limb muscle was measured using AN' ALYZA Immunoassay System human VEGF kit (GENZYME) (FIG. 8).

Figure 9:
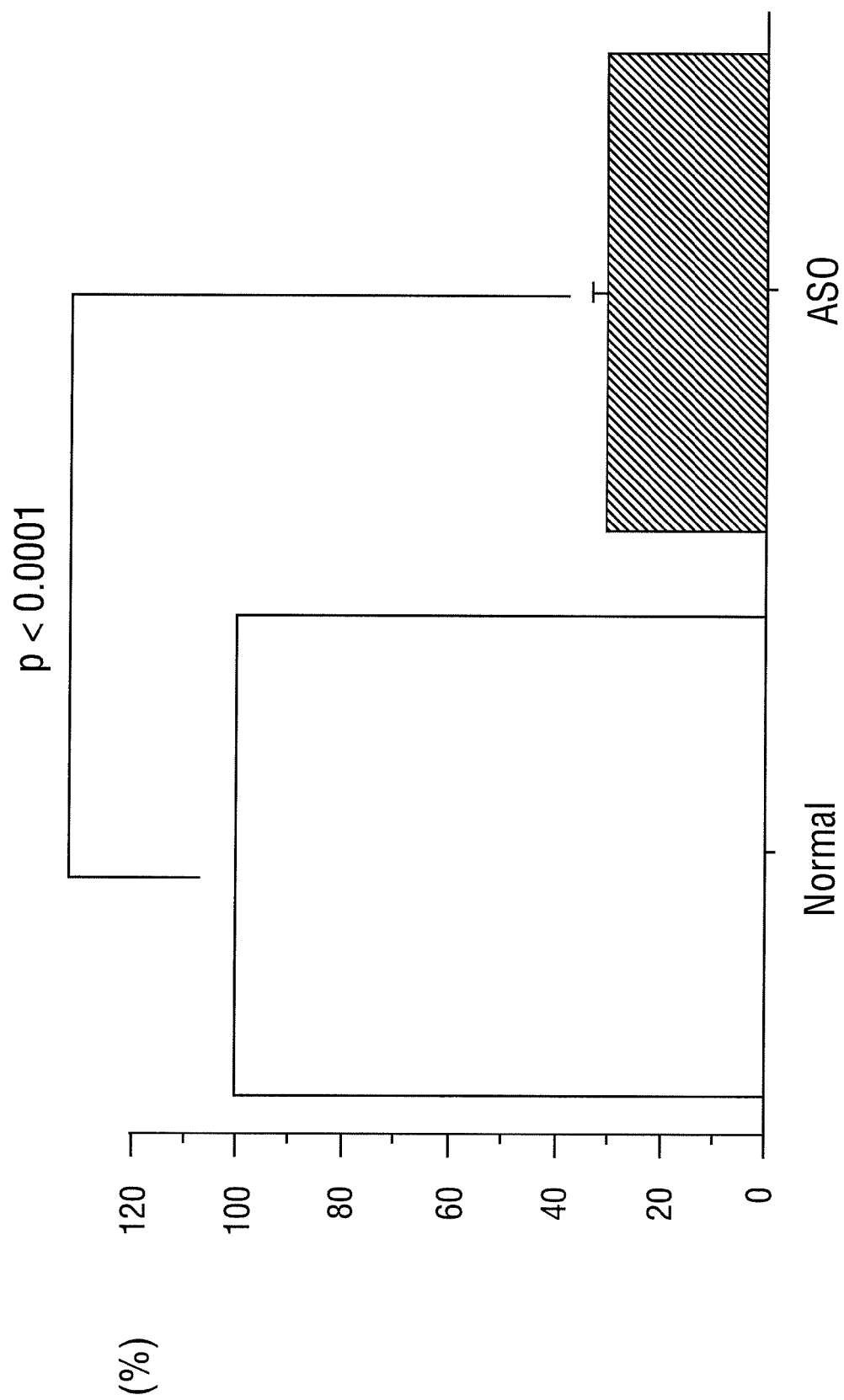
FIG. 9 is a graph showing the blood flow ratio of untreated right hind limb (normal), and left hind limb (ASO), determined by LDI, 10 days after surgery for producing a mouse hind limb ischemia ASO model.
Figure 12:
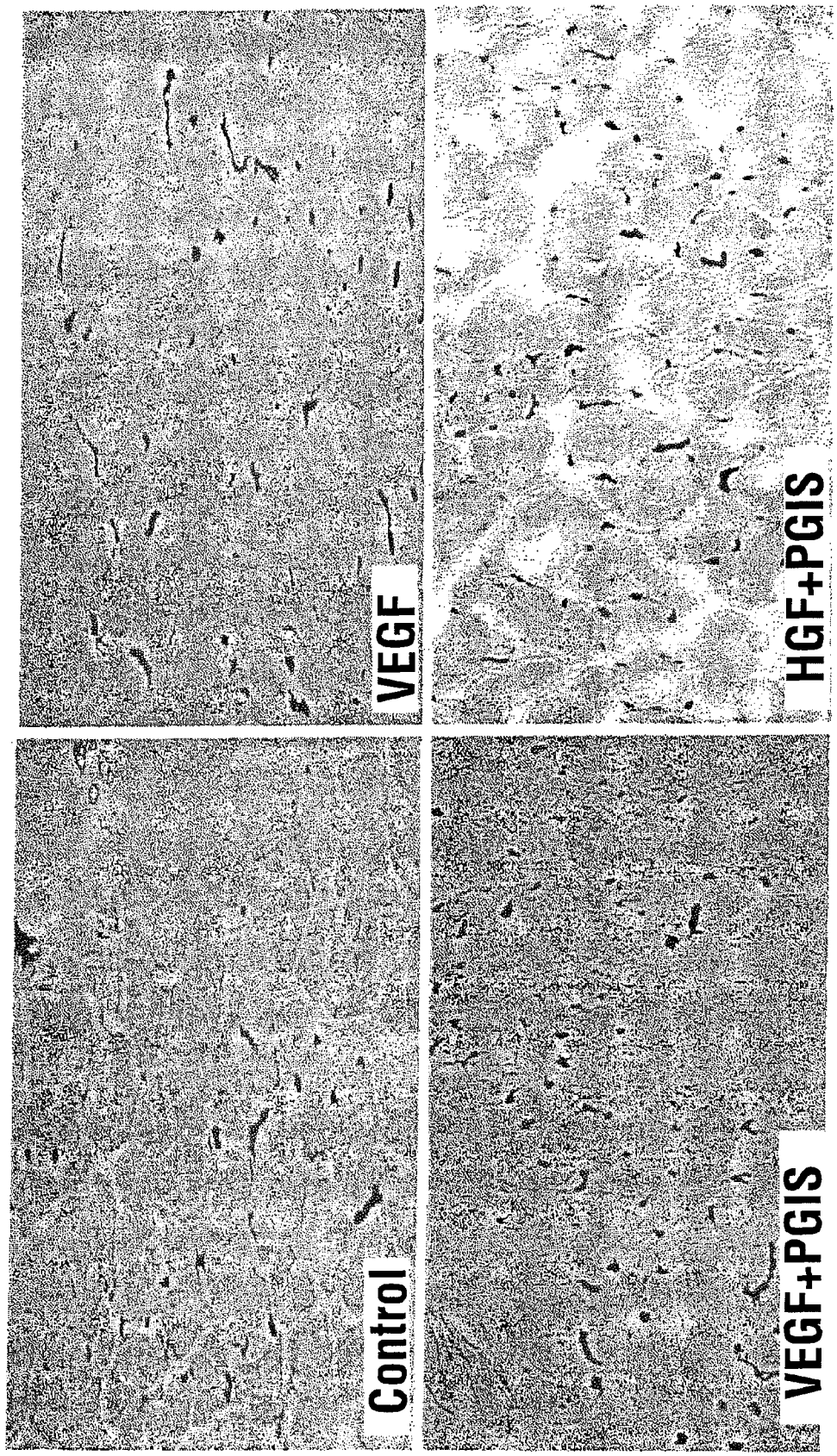
FIG. 12 is a photograph of the frozen sections of the ischemic hind limb muscle stained by alkaline phosphatase staining, 4 weeks after the administration of the PGIS gene and HGF gene, VEGF gene, or VEGF gene and PGIS gene to a mouse hind limb ischemia ASO model.

2. Mouse hind limb ischemia ASO model was produced by a similar method as above. Ten days later, the blood flow in both hind limbs was evaluated using Laser Doppler Imager (LDI, Moor Instruments Ltd, MLDI5070), and the left-right ratio was calculated (FIG. 9; right leg (normal), left hind limb (ASO)). As a result, taking the normal blood flow as 100%, the amount of blood flow in the left hind limb was confirmed to have been decreased to approximately 30% thereof. After the evaluation, 500 .mu.g each of the above-mentioned genes of (1) was administered into the left hind limb muscle in the form of naked plasmids. Four groups were set up: a control group without administration; a group given the VEGF gene alone; a group given the PGIS gene alone; and a group given a combined application of the VEGF gene and PGIS gene. 2 weeks and 4 weeks after the gene administration, the blood flow was evaluated using LDI, and the proportion of increase was calculated. Then, 4 weeks later, the left hind limb muscle was extirpated, and after preparing a frozen section, the intramuscular capillary density was measured by alkaline phosphatase staining (FIG. 12). Significant difference test was performed by the Fisher's PLSD method.

(3) Result

1. As indicated in FIG. 8, no intramuscular concentration of human VEGF protein in the ischemic hind limb was detected in the control and the PGIS gene administered groups, and the concentration was detected to be higher in groups to which the VEGF gene and PGIS gene were administered in combination than the group wherein the VEGF gene was administered alone.

Figure 10:
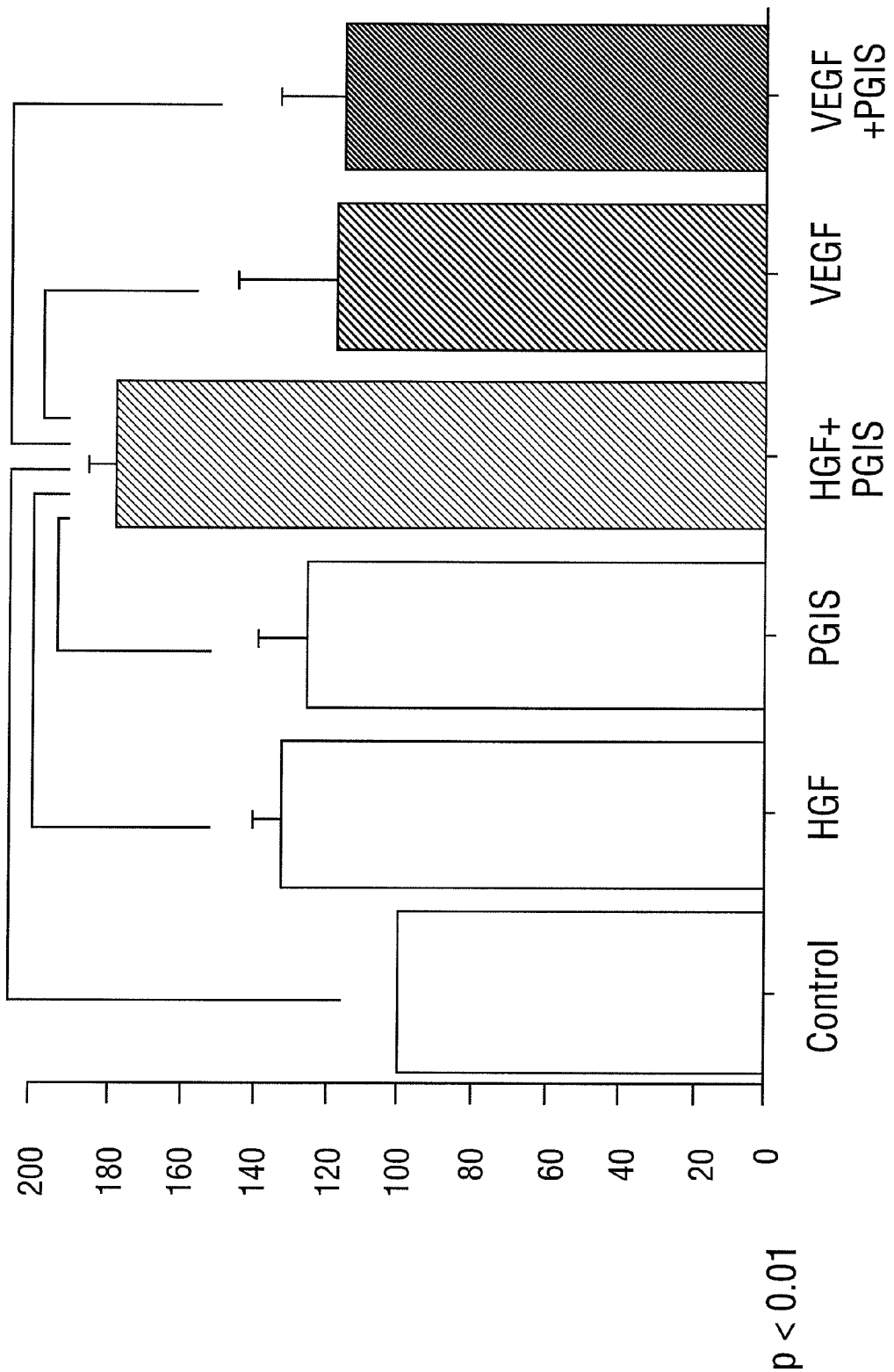
FIG. 10 is a graph showing the result of examination wherein the proportion of increase of the amount of blood flow in the ischemic hind limb muscle was investigated by LDI, 2 weeks after the administration of the PGIS gene, VEGF gene, or VEGF gene and PGIS gene to a mouse hind limb ischemia ASO model.
Figure 11:
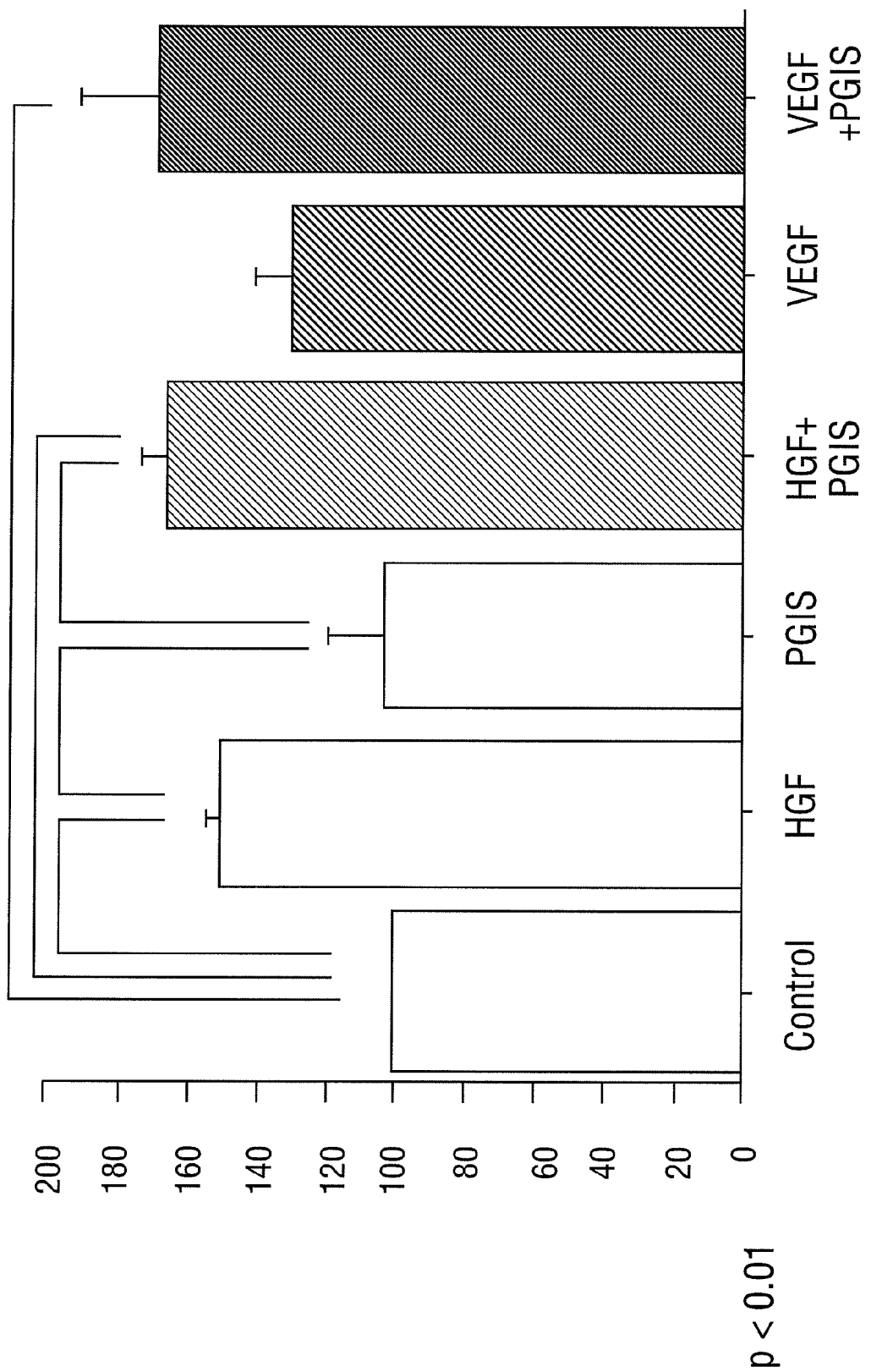
FIG. 11 is a graph showing the result of examination wherein the proportion of increase of the amount of blood flow in the ischemic hind limb muscle was investigated by LDI, 4 weeks after the administration of the PGIS gene, VEGF gene, or VEGF gene and PGIS gene to a mouse hind limb ischemia ASO model.

2. The proportion of increase of blood flow in the left hind limb measured by LDI, 2 weeks later is shown in FIG. 10, and those 4 weeks later is shown in FIG. 11. The blood flow 2 weeks later was not improved, by either the administration of the VEGF gene alone, nor the VEGF gene and PGIS gene in combination. However, 4 weeks later, the blood flow was improved by the administration of the VEGF gene alone, and the VEGF gene and PGIS gene in combination compared to the control group. Unexpectedly, by the combined use of the PGIS gene and VEGF gene, the blood flow was remarkably improved compared to the independent administrations of the genes (2 weeks later: control: 100%, PGIS gene administration: 105%, VEGF gene administration: 117%, VEGF gene+PGIS gene administration: 115%; 4 weeks later: control: 100%, PGIS gene administration: 103%, VEGF gene administration: 130%, VEGF gene+PGIS gene administration: 169%, P<0.01).

Figure 13:
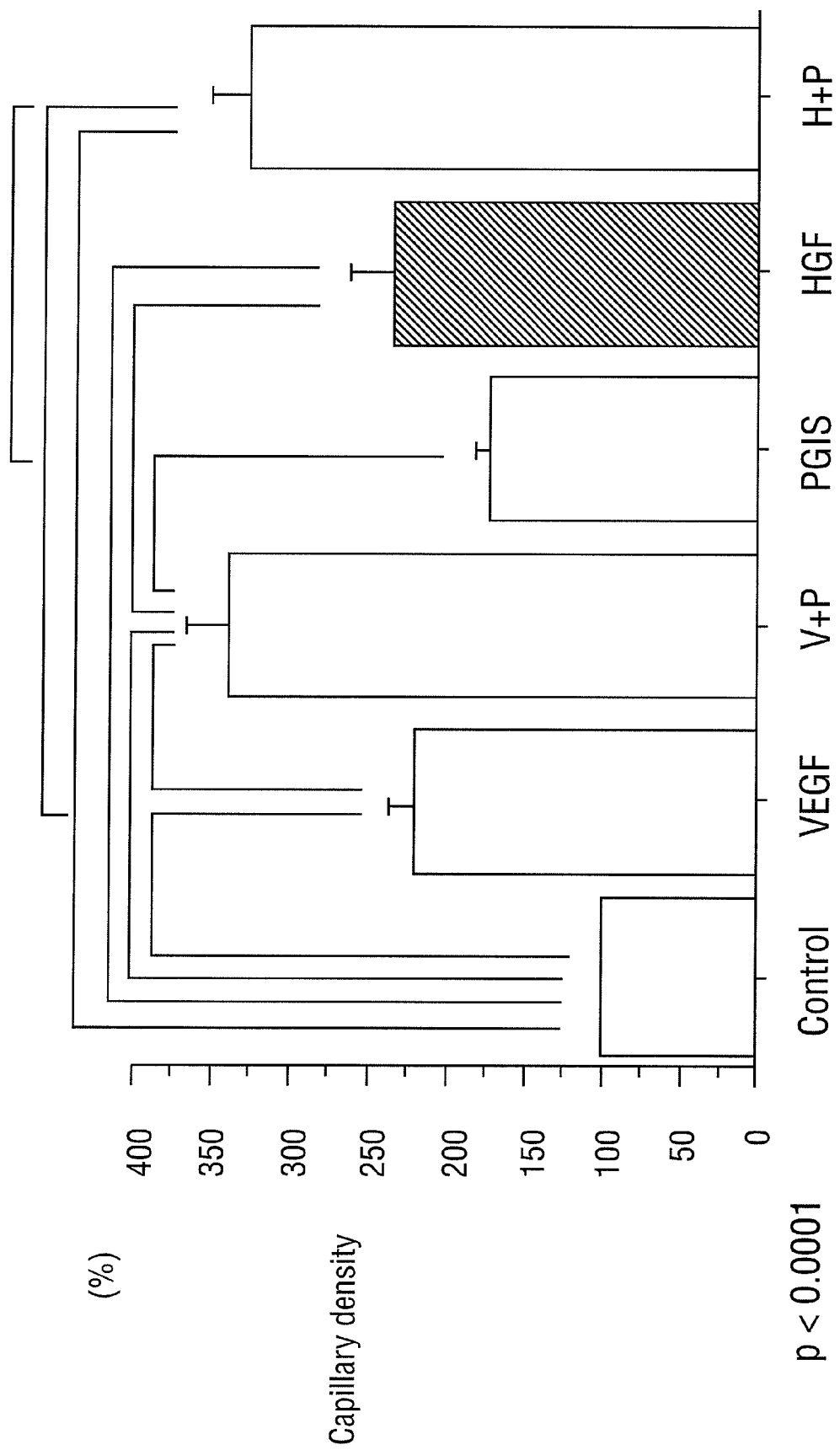
FIG. 13 is a graph showing the result of examination wherein the capillary density was investigated b 4 weeks after the administration of the PGIS gene, VEGF gene, or VEGF gene and PGTS gene to a mouse hind limb ischemia ASO model.

The intramuscular capillary density 4 weeks after the gene administration is shown in FIG. 13. The capillary density increased due to the VEGF gene administration. Furthermore, the combined use of the PGIS gene and VEGF gene remarkably increased the capillary density compared to the independent administration of the genes. (control: 100%, PGTS gene administration: 175%, VEGF gene administration: 221%, VEGF gene+PGIS gene administration: 338%, P<0.0001).

INDUSTRIAL APPLICABILITY

The present invention provides a novel and highly effective pharmaceutical composition for angiogenic therapy which contains as the active ingredients at least one substance selected from the group consisting of substances having vasodilating effect and/or platelet aggregation inhibitory effect, and substances producing them; and a gene encoding an angiogenesis factor. Furthermore, due to the present invention it was newly discovered that genes, such as prostacyclin synthase gene and ets-1 gene, which were not known to be useable for angiogenic therapy can be applied to angiogenic therapy. Finally, pharmaceutical compositions for angiogenic therapy containing these genes as the active ingredients were provided.

What is claimed is:

1. A pharmaceutical composition for angiogenic therapy comprising an ets-1 gene, a gene encoding a hepatocyte growth factor (HGF), and a pharmaceutically acceptable filler.

2. A method for angiogenic therapy, the method comprising administering an ets-1 gene to a patient in need thereof, thereby causing new blood vessel development in the patient.

3. The method for angiogenic therapy of claim 2, wherein the patient suffers from or is at risk of an ischemic disease or arterial disease.

4. The method for angiogenic therapy of claim 3, wherein the ischemic disease or arterial disease is selected from the group consisting of arteriosclerosis obliterans, myocardial infarction, angina pectoris, cardiomyopathy, and cerebrovascular disease.

5. The method for angiogenic therapy of claim 2, further comprising administering another gene encoding an angiogenesis factor.

6. The method for angiogenic therapy of claim 5, wherein each of the genes is present in a different formulation.

7. The method of angiogenic therapy of claim 5, wherein the patient suffers from or is at risk of an ischemic disease or arterial disease.

8. The method of angiogenic therapy of claim 7, wherein the ischemic disease or arterial disease is selected from the group consisting of arteriosclerosis obliterans, myocardial infarction, angina pectoris, cardiomyopathy, and cerebrovascular disease.

9. The method for angiogenic therapy of claim 5 or 6, wherein the angiogenesis factor is HGF.

10. A method for angiogenic therapy, the method comprising administering an ets-1 gene to a patient in need thereof, thereby causing new blood vessel development in the patient.

11. The method of angiogenic therapy of claim 10, wherein the ischemic disease or arterial disease is selected from the group consisting of arteriosclerosis obliterans, myocardial infarction, angina pectoris, cardiomyopathy, and cerebrovascular disease.

12. The method for angiogenic therapy of claim 5 or 6, wherein the angiogenesis factor is vascular endothelial growth factor (VEGF).

* * * * *

UNITED STATES PATENT AND TRADEMARK OFFICE
CERTIFICATE OF CORRECTION

PATENT NO.         : 7,994,151 B2
APPLICATION NO.    : 12/435335
DATED              : August 9, 2011
INVENTOR(S)        : Morishita et al.

It is certified that error appears in the above-identified patent and that said Letters Patent is hereby corrected as shown below:

In Column 36, line 30, claim 10, please delete "A method for angiogenic therapy, the method comprising administering an ets-1 gene to a patient in need thereof, thereby causing new blood vessel development in the patient" and insert --The method of angiogenic therapy of claim 9, wherein the patient suffers from or is at risk of an ischemic disease or arterial disease--.

Signed and Sealed this
Sixth Day of March, 2012

David J. Kappos
*Director of the United States Patent and Trademark Office*